(12) United States Patent
Biel et al.

(10) Patent No.: US 11,672,484 B2
(45) Date of Patent: Jun. 13, 2023

(54) ELECTRODE FALLOFF DETECTION

(71) Applicant: ZOLL Medical Corporation, Chelmsford, MA (US)

(72) Inventors: Eric J Biel, Pittsburgh, PA (US); Ryan D Macel, Glenshaw, PA (US); Timothy J Olczak, Pittsburgh, PA (US); Gary A Freeman, Waltham, MA (US)

(73) Assignee: ZOLL Medical Corporation, Chelmsford, MA (US)

( * ) Notice: Subject to any disclaimer, the term of this patent is extended or adjusted under 35 U.S.C. 154(b) by 1154 days.

(21) Appl. No.: 15/381,206

(22) Filed: Dec. 16, 2016

(65) Prior Publication Data
US 2018/0168508 A1    Jun. 21, 2018

(51) Int. Cl.
*A61B 5/00* (2006.01)
*A61N 1/08* (2006.01)
*A61N 1/04* (2006.01)
*A61B 5/282* (2021.01)
*A61B 5/1455* (2006.01)

(52) U.S. Cl.
CPC .......... *A61B 5/6843* (2013.01); *A61B 5/282* (2021.01); *A61N 1/0404* (2013.01); *A61B 5/14551* (2013.01); *A61B 5/6823* (2013.01); *A61B 5/6831* (2013.01); *A61B 2560/0252* (2013.01); *A61B 2562/0214* (2013.01);
(Continued)

(58) Field of Classification Search
CPC .......... A61B 5/04085; A61B 5/14551; A61B 5/6843; A61B 5/6831; A61B 5/6823; A61B 2562/0257; A61B 2562/0276; A61B 2562/0219; A61B 2560/0252; A61N 1/0404; A61N 2001/083
See application file for complete search history.

(56) References Cited

U.S. PATENT DOCUMENTS 6,075,369 A    6/2000  Morgan
6,253,099 B1   6/2001  Oskin et al.
(Continued)

FOREIGN PATENT DOCUMENTS

WO    WO-2013038285 A1 *  3/2013  ........... A61B 5/0476

OTHER PUBLICATIONS

Lofhede, J., Thordstein, M., Seoane, F., Textile Electrode for EEG Recording, 2012, Sensors, 12, 16907-16919. (Year: 2012).*

*Primary Examiner* — Eun Hwa Kim
(74) *Attorney, Agent, or Firm* — Finch & Maloney PLLC

(57) ABSTRACT

Systems for detecting contact between an electrode and a patient's skin using one or more contact detection schemes are provided. An example system can include an electrode assembly comprising at least one electrode configured to be disposed substantially proximate to the patient's skin and configured to at least one of sense an ECG signal of the patient and provide one or more therapeutic pulses to the patient, one or more sensors disposed on the electrode assembly and isolated from the electrode, the sensors configured to measure one or more properties to determine contact between the electrode and the patient's skin, and a controller configured to receive data representing the measured one or more properties and determine, based at least in part on the received data, whether the electrode is in contact with the patient's skin. The sensors can include temperature, impedance, capacitance, optical, and other similar sensors.

29 Claims, 21 Drawing Sheets

(52) U.S. Cl.
CPC ............ *A61B 2562/0219* (2013.01); *A61B 2562/0257* (2013.01); *A61B 2562/0276* (2013.01)

(56) References Cited

U.S. PATENT DOCUMENTS

| | | |
|---|---|---|
| 7,526,345 B2 | 4/2009 | Covey et al. |
| 8,116,864 B2 | 2/2012 | Covey et al. |
| 8,140,154 B2 | 3/2012 | Donnelly et al. |
| 8,271,082 B2 | 9/2012 | Donnelly et al. |
| 8,656,901 B2 | 2/2014 | Kim et al. |
| 8,676,313 B2 | 3/2014 | Volpe et al. |
| 8,706,215 B2 | 4/2014 | Kaib et al. |
| 9,579,514 B2 | 2/2017 | Freeman et al. |
| 2001/0051821 A1* | 12/2001 | Snyder .................. A61B 5/276 607/142 |
| 2003/0055478 A1 | 3/2003 | Lyster et al. |
| 2014/0051962 A1* | 2/2014 | Krusor ................ A61B 5/7455 600/386 |
| 2015/0005588 A1 | 1/2015 | Herken et al. |
| 2016/0059023 A1* | 3/2016 | Freeman .............. A61N 1/3925 607/8 |
| 2016/0103482 A1 | 4/2016 | Volpe et al. |
| 2016/0270738 A1 | 9/2016 | Volpe et al. |
| 2016/0274162 A1 | 9/2016 | Freeman et al. |
| 2016/0325108 A1 | 11/2016 | Volpe et al. |
| 2017/0056650 A1* | 3/2017 | Cohen ................ A61B 5/0408 |

\* cited by examiner

ELECTRODE FALLOFF DETECTION

BACKGROUND

The present disclosure is directed to a wearable medical device, and more specifically, to a wearable medical device configured to detect a falloff event associated with one or more electrodes.

There are a wide variety of electronic and mechanical devices for monitoring and treating patients' medical conditions. In some examples, depending on the underlying medical condition being monitored or treated, medical devices such as cardiac monitors or defibrillators may be surgically implanted or externally connected to the patient. In some cases, physicians may use medical devices alone or in combination with drug therapies to treat conditions such as cardiac arrhythmias.

One of the deadliest cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a patient in which various arrhythmias of the heart, such as ventricular fibrillation, ventricular tachycardia, pulseless electrical activity (PEA), and asystole (heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the patient. The sooner these resuscitation efforts begin, the better the patient's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the patient's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the patient's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus also available from ZOLL Medical Corporation.

SUMMARY

In certain implementations, a system can be provided for detecting contact between an electrode and a patient's skin. The system can include an electrode assembly comprising at least one electrode configured to be disposed substantially proximate to the patient's skin and configured to at least one of sense an ECG signal of the patient and provide one or more therapeutic pulses to the patient; one or more sensors disposed on the electrode assembly and isolated from the electrode, the one or more sensors configured to measure one or more properties to determine contact between the electrode and the patient's skin; and a controller configured to receive data representing the measured one or more properties and determine, based at least in part on the received data, whether the electrode is in contact with the patient's skin.

In certain implementations, the system can further include an alarm module operably configured to the controller and configured to output at least one alarm if the controller determines that the electrode is not in contact with the patient's skin. In some examples, the at least one alarm can include at least one of an audio alarm, a visual alarm, a tactile alarm, and combinations thereof.

In certain implementations, the system can further include a network interface operably connected to the controller and configured to establish communication between the controller and a remote computing device such that, if the controller determines that the electrode is not in contact with the patient's skin, a notification is sent to the remote computing device indicating an electrode falloff event.

In certain implementations, the one or more sensors can be disposed on the electrode. In some examples, the electrode can include an electrode configured to sense at least one surface ECG signal, wherein the electrode can include an impedance detection range selected from at least one of 50Ω-200 Ω, 200Ω-400 Ω, 400Ω-10 kΩ, 10 kΩ-1 MΩ, and 1 MΩ-10 MΩ.

In certain implementations, the one or more properties define a level of contact between the electrode and the patient's skin. In some examples, the controller can be further configured to compare the level of contact to a contact threshold level of contact to determine a falloff event.

In certain implementations, the one or more sensors are configured to measure an impedance level between the electrode and the patient's skin. In some examples, the controller can be further configured to model an electrical circuit representative of an interface between the one or more sensing locations and the patient's skin based at least upon the measured impedance level, and determine whether the electrode is in contact with the patient's skin. In some examples, the modeled electrical circuit can be configured to simulate an impedance level between the electrode assembly and the patient's skin, the modeled electrical circuit comprising at least a first cell configured to simulate a stored energy level of the electrode, a first capacitive and resistive pair configured to simulate the electrode, a second capacitive and resistance pair configured to simulate an electrolyte layer positioned between the electrode and the patient's skin, a second cell configured to simulate an energy potential between the electrode and the patient's skin, a second capacitive and resistance pair configured to simulate an epidermis layer of the patient, and a resistance configured to simulate a dermis layer of the patient.

In certain implementations, the one or more properties can include at least one of temperature, capacitance, measured distance between the electrode and the patient's body, and oxygen saturation of the patient's blood.

In certain implementations, the one or more sensors can include a combination of multiple sensor types selected from at least a temperature sensor, a capacitive sensor, and an optical sensor. In some examples, the multiple sensor types can be configured to operate in concert to provide multiple measurements of the one or more properties determined by the position of the electrode in relation to the patient's body. In some examples, the controller can be further configured to receive data representing the measured one or more properties from each of the multiple sensor types to determine whether the electrode is in contact with the patient's body.

In certain implementations, a wearable medical system can be provided for detecting contact between an electrode and a patient's skin. The wearable medical system can include an externally wearable cardiac monitoring device; an electrode configured to be coupled to the externally wearable cardiac monitoring device and configured to be disposed substantially proximate to the patient's skin to at least one of sense an ECG signal of the patient and provide one or more therapeutic pulses to the patient; at least one temperature sensor disposed on the electrode, the at least one temperature sensor to measure a value indicative of a temperature at an interface of the electrode and the patient's skin; and a controller housed within the externally wearable cardiac monitoring device, the controller configured to receive data representing the measured value and determine, based at least in part on the received data, whether the electrode is in contact with the patient's skin.

In certain implementations of the wearable medical system, the at least one temperature sensor can be disposed on a first surface of the electrode positioned substantially proximate to the patient's skin, the medical system further comprising a second temperature sensor disposed on a second surface of the electrode and configured to be positioned away from the patient's skin, the second temperature sensor configured to measure ambient temperature.

In certain implementations of the wearable medical system, the controller can be configured to determine whether the electrode is in contact with the patient's body based on a determination of whether the measured temperature has changed faster than a threshold rate of change.

In certain implementations of the wearable medical system, the controller can be configured to determine whether the electrode is in contact with the patient's body based on a determination of whether the measured temperature has exceeded, for at least a threshold period of time, a threshold of temperature change from an expected temperature.

In certain implementations of the wearable medical system, the wearable medical system can further include an ambient temperature sensor configured to measure ambient temperature, wherein the controller is configured to receive data representing the ambient temperature.

In certain implementations of the wearable medical system, the wearable medical system can further include an accelerometer to measure motion associated with the sensing electrode, wherein the controller is configured to receive data representing the measured motion.

In certain implementations of the wearable medical system, the at least one temperature sensor can include at least one of a thermocouple, a thermistor, a resistance temperature detector, a pyrometer, and an infrared temperature sensor.

In certain implementations of the wearable medical system, the at least one temperature sensor can be thermally insulated from a surface of the electrode. In some examples, the wearable medical system can further include an insulating material positioned between the at least one temperature sensor and the surface of the electrode to thermally insulate the at least one temperature sensor.

In certain implementations, a medical system for detecting contact between an electrode and a patient's skin is provided. The system includes an externally wearable cardiac monitoring system; an electrode configured to be coupled to the externally wearable cardiac monitoring device and configured to be disposed substantially proximate to the patient's skin and configured to at least one of sense an ECG signal of the patient and provide one or more therapeutic pulses to the patient; at least one capacitive sensor disposed on the electrode and configured to be positioned substantially proximate the patient's skin to measure a capacitance value between an interface of the electrode and the patient's skin; and a controller housed within the externally wearable cardiac monitoring device, the controller configured to receive data representing the measured capacitance value and determine, based at least on the received data, whether the electrode is in contact with the patient's skin. In some examples, the one or more sensing locations configured to measure capacitance can include at least one of a dielectric-based capacitive sensor, an electrostatic-based touch panel, and a resistive-based capacitance sensor.

In certain implementations, an alternative medical system for detecting contact between an electrode and a patient's skin is provided. The system includes an externally wearable cardiac monitoring system; an electrode configured to be coupled to the externally wearable cardiac monitoring device and configured to be disposed substantially proximate to the patient's skin and configured to at least one of sense an ECG signal of the patient and provide one or more therapeutic pulses to the patient; at least one optical sensor disposed on the electrode and configured to be positioned substantially proximate the patient's skin and to measure a value indicative of a distance between the electrode and the patient's skin; and a controller housed within the externally wearable cardiac monitoring device, the controller configured to receive data representing the measured value indicative of the distance between the electrode and the patient's skin and determine, based at least on the received data, whether the electrode is in contact with the patient's skin. In some examples, the one or more sensing locations configured to optically measure a distance between the electrode and the patient's body can include at least one of a photoelectric sensor, an infrared proximity sensor, and a pulse oximetry sensor. In some examples, the pulse oximetry sensor can be configured to measure blood oxygen saturation information for the patient.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
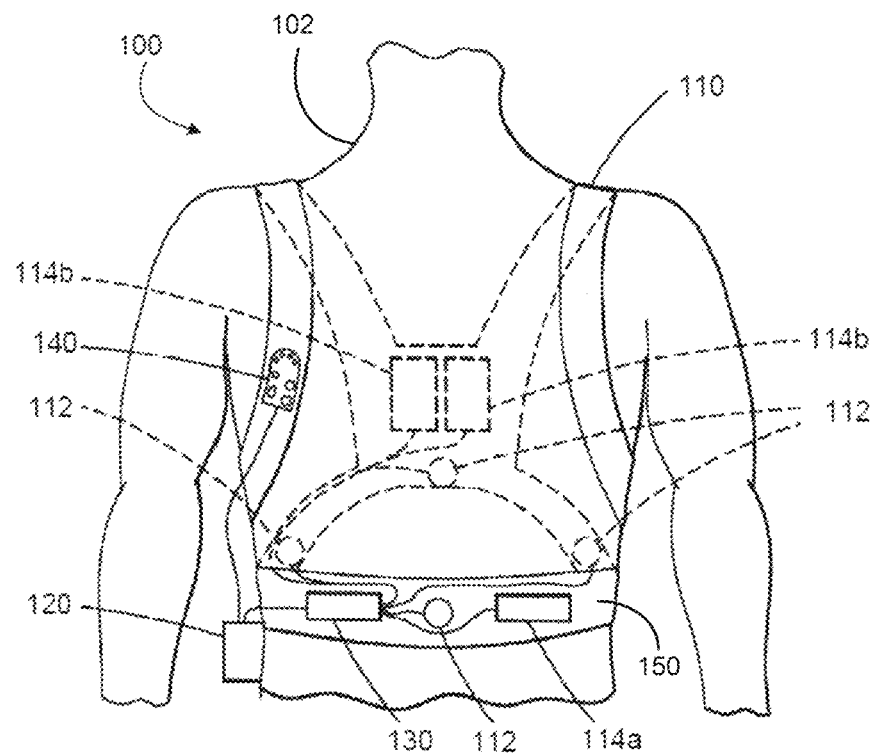
FIG. 1 depicts a wearable medical device, in accordance with an example of the present disclosure.

This disclosure relates to improvements in detecting that electrodes associated with a wearable medical device are in contact with a patient's skin prior to, for example, delivering a therapy, or to maintain a good connection for monitoring one or more physiological signals of the patient.

Medical devices as described herein include cardiac monitoring and/or therapeutic devices as described in further detail below. For both therapeutic and monitoring medical devices, maintaining one or more electrodes in their proper positions results in effective operation of the medical devices than when the one or more electrodes are not properly positioned. Such electrodes are "dry" electrodes, e.g., electrodes that are not attached to the patient's skin by an adhesive or where contact is mediated by conductive gel. Typically, a dry electrode is placed directly on the skin and, as a result of the contact between the electrode and the skin, perspiration can accumulate on the electrode surface to provide an electrolytic connection with the patient. A dry electrode can be constructed from a housing configured to hold various circuit components and a treated, anodized metal surface configured to contact the patient's skin. For example, the treated, anodized metal surface can be treated with a tantalum pentoxide coating.

Depending on the design, a dry electrode can be configured to have a wide range of input impedances when in contact with a patient's skin. For example, the impedance as seen by the electrodes when in contact with the patient's skin can be in excess of 400 ohms, typically in the range of tens to hundreds of mega ohms. In certain implementations, the dry electrodes can have an impedance range of 400Ω to 10 MΩ. In some examples, a dry electrode can be a high impedance electrode having an impedance range of 10 MΩ to 100 MΩ, 100 MΩ to 1 GΩ, and 1 GΩ to 10 GΩ. It should be noted that these impedance ranges are provided by way of example only and can be configured based upon the design, manufacture, and intended use of the electrodes.

With such a design, having a high impedance range, by using a high frequency signal (e.g., 1 kHz-100 kHz) with a micro-current signal (e.g., 10 μA), the impedance value measured by the electrode will increase above, for example, 10 MΩ when the electrode loses contact with the patient's skin.

Additionally, the dry electrode can be configured such that it operates at a specific frequency range at a specific set of current densities. For example, the input signal to the dry electrode can have a frequency ranging from 0.5 Hz to 200 Hz, 1 Hz to 100 Hz, 10 Hz to 1 kHz, 10 kHz to 100 kHz, and various other input frequency ranges. Similarly, the electrode can be configured to operate at various current densities. For example, a dry electrode can have a contact surface area of approximately 10 $cm^2$ and an input current of approximately 10 μA. As such, the current density would be approximately 1 μA/$cm^2$. However, it should be noted that this current density is shown by way of example only and an electrode can be configured to operate at various other frequency densities. For example, the electrode can be configured to operate at 0.1 μA/$cm^2$-1.5 μA/$cm^2$, 1.5 μA/$cm^2$-2.5 μA/$cm^2$, 2.5 μA/$cm^2$-5 μA/$cm^2$, 5 μA/$cm^2$-10 μA/$cm^2$, and other similar frequency densities.

In certain implementations, when a dry electrode is properly positioned on a patient, a conductive surface of the electrode faces the patient and directly or indirectly (e.g., through an intervening conductive mesh or other conductive surface) contacts the patient's skin. When properly positioned, a therapy electrode (e.g., as included in a therapeutic medical device) can apply a therapy, such as a defibrillation shock, to the patient. Similarly, when properly positioned, a sensing electrode (e.g., as included in both therapeutic and monitoring medical devices) can measure various physiological signals including, but not limited to, ECG signals, heart sounds, tissue fluid levels, lung sounds, respiration sounds, patient movement, and other similar physiological signals of the patient. Due to, for example, patient motion or improper installation by the patient, health care provider, or other professional, an electrode can sometimes be or become improperly positioned over time. As a result, an electrode's conductive surface may not make optimum contact with the patient. A portion of an electrode can pull away from the patient's skin, resulting in a reduced contact area with the patient's skin. For example, a sensing electrode can become detached from the garment or the garment can become twisted or otherwise pulled away from the patient's skin. Such conditions can result in a falloff event where the sensing electrode partially (e.g., where a portion of a sensing electrode has lost contact with the patient's skin) or fully pulls away from the patient's skin. In such a falloff event, the quality of information being monitored by the sensing electrode can be reduced or, if the sensing electrode has lost all contact with the skin, can be reduced to zero. In a sensing electrode falloff event, a loss of contact with the patient's skin can result in lower quality sensed electrocardiogram signals. In a therapy electrode falloff event, a loss of contact with the patient's skin can increase an electrode impedance and result in a less effective therapeutic shock.

As described herein, various techniques for detecting electrode falloff can be used. For example, a temperature-based falloff detection scheme can be used. One or more temperature sensors can be integrated into the electrodes. Output from the temperature sensors can be processed (e.g., conditioned and filtered) prior to a medical device controller receiving the temperature sensor outputs for further processing. Measured changes in an interface between the electrode and the patient's skin can be further evaluated to determine if a falloff event has occurred, e.g., has an electrode lost contact with the patient's skin.

Another technique can be a capacitance-based falloff detection scheme. One or more capacitance or touch sensors can be integrated into the electrodes. The medical device controller can monitor the capacitance sensor outputs for the electrodes to detect an electrode falloff, e.g., when some or all of the conductive portion of the sensing electrode loses contact with the patient's skin. For example, the capacitance sensors can be configured to receive an input capacitance from a patient's body through contact between the patient's skin and the capacitance sensor mounted in an electrode. The medical device controller can receive a capacitive falloff signal including the capacitance change information, process the information to determine that the sensor has likely fallen off, and provide a notification to a patient that the sensor has likely fallen off.

An optical-based falloff detection scheme can be included in a wearable medical device for detecting electrode falloff. In such a scheme, one or more optical sensors can be integrated into the electrodes. The medical device controller can monitor the optical sensor outputs to detect an electrode falloff e.g., when some or all of the conductive portion of the sensing electrode loses contact with the patient's skin. For example, the optical sensors can be configured to both emit an optical signal and receive a reflected signal from the patient's skin. By analyzing properties of the received signal, and comparing the received signal to the transmitted signal, a processing circuit can determine a distance measurement between the optical sensor and the patient's skin. The medical device controller, or a component of the medical device controller such as the electrode falloff detector, can receive an optical falloff signal including distance measurement and change information, process the information to determine whether the sensor has likely fallen off, and provide a notification to a patient that the sensor has likely fallen off.

In another example, an impedance-based falloff detection scheme can be included in a wearable medical device. In such a scheme, resistance measuring properties of an electrode can be used to measure changes in impedance and/or capacitance between an electrode-skin interface, e.g., the area of contact between the sensing and/or therapy electrode and a patient's skin. In such an example, the medical device controller can monitor the outputs of each sensing electrode to determine changes in impedance that could be indicative of a falloff event, e.g., when some or all of the conductive portion of the electrode loses contact with the patient's skin.

Examples of measuring capacitance and impedance in a patient using electrodes can be found in U.S. patent application Ser. No. 14/843,843, titled "Impedance Spectroscopy for Defibrillator Applications," filed Sep. 2, 2015, the content of which is incorporated herein by reference in its entirety. Such techniques as described therein can be incorporated into the detection schemes as described in the present disclosure.

Various aspects and embodiments as described herein are directed to a wearable monitoring and/or therapeutic device that can be fully or partially worn by, for example, an ambulatory patient. A wearable therapeutic device can include a garment with one or more pockets configured to house at least one therapy electrode. The garment can also include one or more attachment points configured to releaseably hold at least one sensing electrode. For example, the attachment point, and a corresponding sensing electrode, can use a hook-and-loop fastener to releaseably attach the sensing electrode to the attachment point. In certain implementations, the therapy electrodes and/or the sensing electrodes can be attached directly to the patient using, for example, a long-term adhesive.

Example Wearable Therapeutic Device

FIG. 1 illustrates an example medical device 100 that is external, ambulatory, and wearable by a patient 102, and configured to implement one or more configurations described herein. For example, the medical device 100 can be a non-invasive medical device configured to be located substantially external to the patient. Such a medical device 100 can be, for example, an ambulatory medical device that is capable of and designed for moving with the patient as the patient goes about his or her daily routine. For example, the medical device 100 as described herein can be bodily-attached to the patient such as the LifeVest® wearable cardioverter defibrillator available from ZOLL® Medical Corporation. In one example scenario, such wearable defibrillators can be worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses.

The medical device 100 can include one or more of the following: a garment 110, one or more sensing electrodes 112 (e.g., ECG electrodes), one or more therapy electrodes 114a and 114b (collectively referred to herein as therapy electrodes 114), a medical device controller 120, a connection pod 130, a patient interface pod 140, a belt 150, or any combination of these. In some examples, at least some of the components of the medical device 100 can be configured to be affixed to the garment 110 (or in some examples, permanently integrated into the garment 110), which can be worn about the patient's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110. Additionally, the therapy electrodes 114 can include one or more conductive gel deployment devices such as the devices described herein and, as other examples, devices described in U.S. Patent Application Publication No. 2015/0005588 entitled "Therapeutic Device Including Acoustic Sensor," the content of which is incorporate herein by reference.

Component configurations other than those shown in FIG. 1 are possible. For example, the sensing electrodes 112 can be configured to be attached at various positions about the body of the patient 102. The sensing electrodes 112 can be operatively coupled to the medical device controller 120 through the connection pod 130. In some implementations, the sensing electrodes 112 can be adhesively attached to the patient 102. In some implementations, the sensing electrodes 112 and at least one of the therapy electrodes 114 can be included on a single integrated patch and adhesively applied to the patient's body.

The sensing electrodes 112 can be configured to detect one or more cardiac signals. Examples of such signals include ECG signals and/or other sensed cardiac physiological signals from the patient. In certain implementations, the sensing electrodes 112 can include additional components such as accelerometers, acoustic signal detecting devices, and other measuring devices for recording additional parameters. For example, the sensing electrodes 112 can also be configured to detect other types of patient physiological parameters and acoustic signals, such as tissue fluid levels, heart sounds, lung sounds, respiration sounds, patient movement, etc. Example sensing electrodes 112 include a metal electrode with an oxide coating such as tantalum pentoxide electrodes, as described in, for example, U.S. Pat. No. 6,253,099 entitled "Cardiac Monitoring Electrode Apparatus and Method," the content of which is incorporate herein by reference.

In some examples, the therapy electrodes 114 can also be configured to include sensors configured to detect ECG signals as well as other physiological signals of the patient. The connection pod 130 can, in some examples, include a signal processor configured to amplify, filter, and digitize these cardiac signals prior to transmitting the cardiac signals to the medical device controller 120. One or more of the therapy electrodes 114 can be configured to deliver one or more therapeutic defibrillating shocks to the body of the patient 102 when the medical device 100 determines that such treatment is warranted based on the signals detected by the sensing electrodes 112 and processed by the medical device controller 120. Example therapy electrodes 114 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device as a means to convert the therapeutic medical device into a monitoring medical device for a specific use (e.g., for operating in a monitoring-only mode) for a patient. Alternatively, the optional therapeutic elements can be deactivated (e.g., by means of a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Example Patient Monitoring Device

The wearable medical device can be a non-therapeutic patient monitoring device for an ambulatory patient, such as cardiac event monitoring (CEM) device or mobile cardiac telemetry (MCT) device. Such devices collect cardiac information, such as a patient electrocardiogram (ECG) data, and provide the information to an external network or remote server on a periodic basis. In some implementations, such devices can also record ECG data associated with a particular triggering event (e.g., an automatically detected cardiac event or a patient reported symptom), and send such data to a remote server for analysis. MCT devices can further comprise additional sensors for measuring non-ECG physiological parameters. Data from non-ECG sensors can be provided along with ECG recordings for identified events.

Cardiac monitoring devices can be used for monitoring patient cardiac function for a predetermined interval (e.g., a number of days or weeks) to provide information about frequency and duration of cardiac events experienced by a patient. Cardiac events that can be identified by patient monitors can include, without limitation, one or more of atrial fibrillation, bradycardia, tachycardia, atrio-ventricular block, Lown-Ganong-Levine syndrome, atrial flutter, sino-atrial node dysfunction, cerebral ischemia, syncope, atrial pause, and/or heart palpitations. The collected information about identified cardiac events can be used, for example, to produce patient reports for time periods of interest.

A patient monitor (e.g., a cardiac monitor) can include a controller, similar to the controller 120 as shown in FIG. 1, though without operably connected therapeutic components such as, for example, therapy electrodes 114 as shown in FIG. 1. The patient monitor controller can be communicatively coupled (e.g., wired or wirelessly coupled) to sensors and/or electrodes appropriately positioned on patient to obtain signals (e.g., ECG data and/or heart sounds data from an acoustic sensor) indicative of cardiac activity. In some examples, the patient monitor controller can, in addition to cardiac monitoring, perform monitoring of other relevant patient parameters, e.g., weight, glucose levels, blood oxygen levels, and blood pressure. The patient monitor controller can also comprise motion sensors to track patient movement. In some examples, the patient monitor can be in the form of an application on a handheld device, such as a smartphone, a personal digital assistant, or a tablet device.

The patient monitor can also include a physiological data processing component for collecting and conditioning the physiological data prior to storing the data locally at computer-readable storage media on the monitor itself and/or transmitting the data to a remote server or device. In some examples, the patient monitor controller can further include a user interface module that allows the patient to manually enter information about a patient condition, and to initiate sending information to the remote server.

Example Medical Device Controller

Figure 2A:
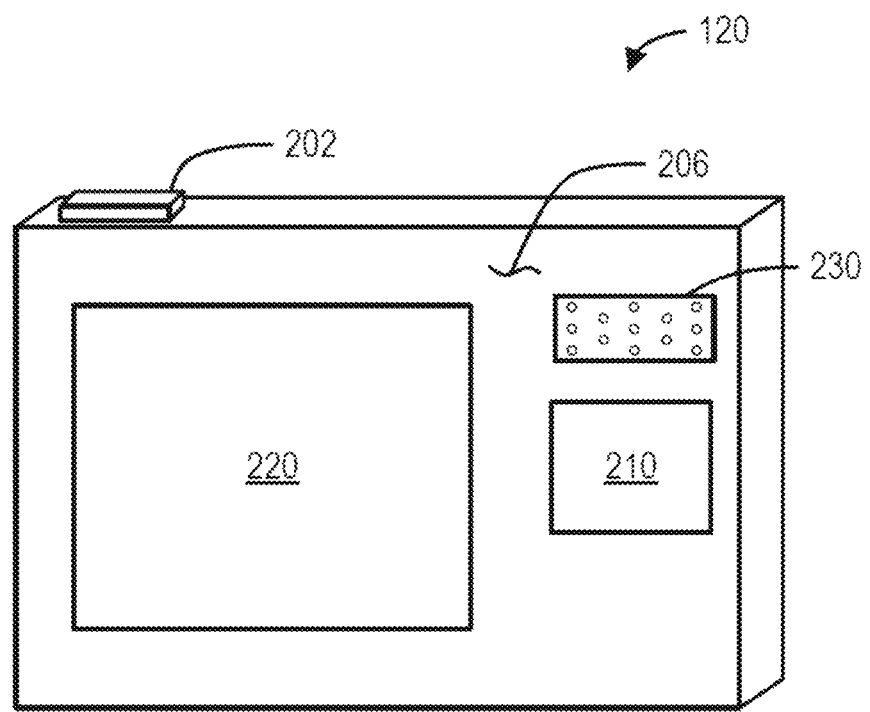
FIGS. 2A and 2B depict front and back views of a medical device controller, in accordance with an example of the present disclosure.
Figure 2B:
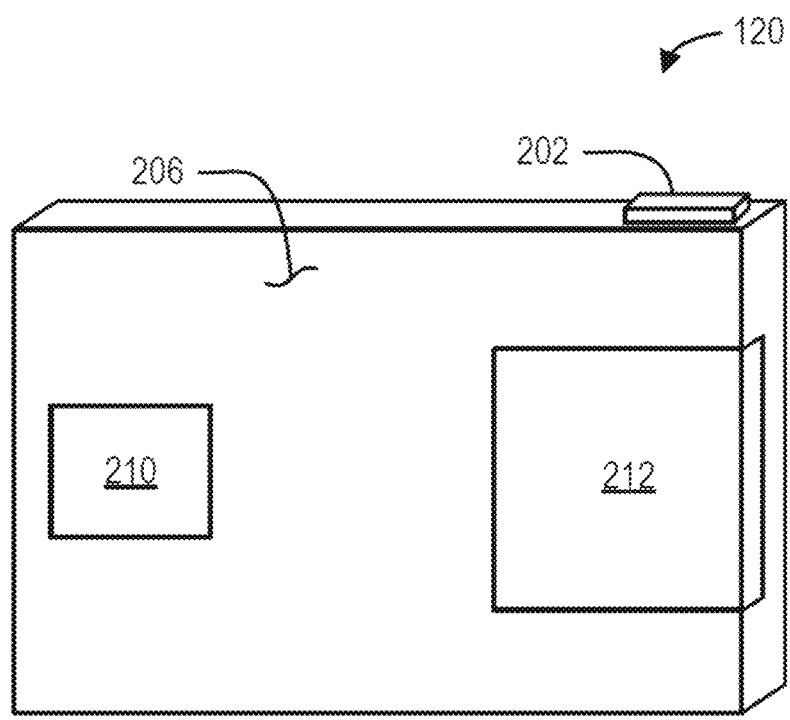

FIGS. 2A-2B illustrate an example of the medical device controller 120. The controller 120 can be powered by a rechargeable battery 212. The rechargeable battery 212 can be removable from a housing 206 of the medical device controller 120 to enable a patient and/or caregiver to swap a depleted (or near depleted) battery 212 for a charged battery. The controller 120 includes a user interface such as a touch screen 220 that can provide information to the patient, caregiver, and/or bystanders. The patient and/or caregiver can interact with the touch screen 220 to control the medical device 100. The controller 120 also includes a speaker 230 for communicating information to the patient, caregiver, and/or the bystander. The controller 120 includes one or more response buttons 210. In some examples, when the controller 120 determines that the patient is experiencing cardiac arrhythmia, the speaker 230 can issue an audible alarm to alert the patient and bystanders to the patient's medical condition. In some examples, the controller 120 can instruct the patient to press and hold one or both of the response buttons 210 to indicate that the patient is conscious, thereby instructing the medical device controller 120 to withhold the delivery of therapeutic defibrillating shocks. If the patient does not respond to an instruction from the controller 120, the medical device 100 can determine that the patient is unconscious and proceed with the treatment sequence, culminating in the delivery of one or more defibrillating shocks to the body of the patient. The medical device controller 120 can further include a port 202 to removably connect sensing devices (e.g., the sensing electrodes 112) and/or therapeutic devices (e.g., the therapy electrodes 114) to the medical device controller 120 (e.g., via the connection pod 130).

Figure 3:
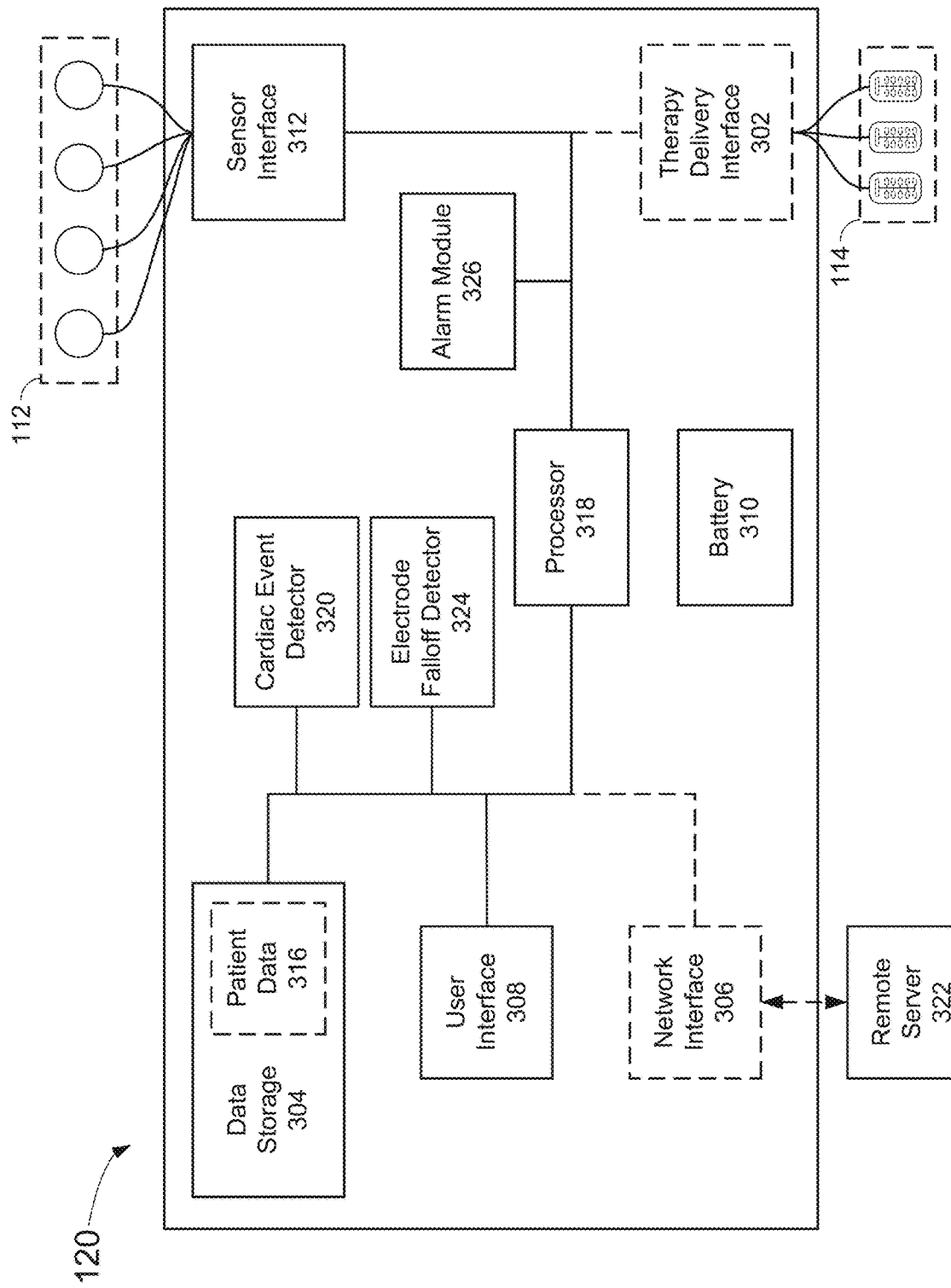
FIG. 3 depicts a component schematic of a sample medical device controller, in accordance with an example of the present disclosure.

FIG. 3 shows a schematic of an example of the medical device controller 120 of FIGS. 1, 2A, and 2B. The controller 120 includes at least one processor 318, a sensor interface 312, an optional therapy delivery interface 302, data storage 304 (which can include patient data storage 316), an optional network interface 306, a user interface 308 (e.g., including the touch screen 220 shown in FIG. 2A), and a battery 310. The sensor interface 312 can be coupled to any one or combination of sensors to receive information indicative of patient parameters. For example, the sensor interface 312 can be coupled to one or more sensing devices including, for example, the sensing electrodes 112. The therapy delivery interface 302 (if included) can be coupled to one or more electrodes that provide therapy to the patient including, for example, the therapy electrodes 114. In some implementations, the therapy delivery interface 302 can also be coupled to pacing electrodes and/or transcutaneous electrical nerve stimulation (TENS) electrodes. The sensor interface 312 and the therapy delivery interface 302 can implement a variety of coupling and communication techniques for facilitating the exchange of data between the sensors and/or therapy delivery devices and the controller 120.

In some examples, the network interface 306 can facilitate the communication of information between the controller 120 and one or more other devices or entities over a communications network. For example, the network interface 306 can be configured to communicate with a remote computing device (e.g., a remote server 322) where a caregiver can access information related to the patient. In certain implementations, the network interface 306 can be configured to establish a wireless connection with the remote computing device. For example, the network interface can be configured to connect to a bridge device such as a wireless router via a local area network such as a WiFi network to establish communications with the remote computing device.

In some examples, the medical device controller 120 includes a cardiac event detector 320 to monitor the cardiac activity of the patient and identify cardiac events experienced by the patient based on received cardiac signals. In some examples, the cardiac event detector 320 can access patient templates (e.g., which can be stored in the data storage 304 as patient data 316) that can assist the cardiac event detector 320 in identifying cardiac events experienced by the particular patient.

In some implementations, the processor 318 includes one or more processors that each can perform a series of instructions that result in manipulated data and/or control the operation of the other components of the controller 120. An example processor architecture can be found in U.S. Patent Application Publication No. 2016/0103482 filed Dec. 18, 2015 and entitled "System and Method for Conserving Power in a Medical Device," the content of which is hereby incorporate by reference in its entirety.

During operation of a medical device (e.g., a therapeutic medical device and/or a monitoring medical device), maintaining a good connection between the electrodes and the patient's skin can result in higher quality monitoring signals received from sensing electrodes as well as providing for higher quality therapy (e.g., defibrillation or pacing shocks) delivered to the patient. As such, various techniques for monitoring for electrode falloff can be utilized with a wearable medical device. Referring again to FIG. 3, the medical device controller 120 can further include an electrode falloff detector 324 configured to monitor for and identify electrode falloff during operation of the wearable medical device. The medical device controller can cause one or more electrodes (e.g., the therapy electrodes 114) to provide an electromagnetic signal (e.g., in the form of an 800 Hz square wave) onto the patient. One or more electrodes (e.g., the sensing electrodes) can detect the signal as it passes through the patient's body. The electrode falloff detector 324 can read the detected signal. In certain implementations, the sensed signal is present only when the transmitting electrodes are in contact with the patient. If an electrode is off of the patient, the value detected by the receiving electrodes and read by the medical device controller will be approximately 0V for that particular transmitting electrode. Thus, in some implementations, the medical device controller can transmit the electromagnetic signal from each of the therapy electrodes in sequence. The electrode falloff detector 324 can then monitor each of the sensing electrodes to confirm that each sensing electrode has received the electromagnetic signal. If, for example, a particular sensing electrode does not receive an electromagnetic signal that the other sensing electrodes are detecting, the medical device controller can determine that the sensing electrode (that did not receive the signal) has fallen off the patient. Similarly, if the medical device controller instructs a therapy electrode to transmit an electromagnetic signal, and no sensing electrodes receive the electromagnetic signal, the electrode falloff detector 324 can determine that the therapy electrode transmitting the signal has fallen off the patient. As such, by stepping through the various electrodes, the medical device controller can continually monitor for electrode falloff.

It should be noted that, in the above example, the therapy electrodes were transmitting the electromagnetic signal, and the sensing electrodes were receiving the electromagnetic signal, by way of example only. In certain implementations, the sensing electrodes can be configured to transmit an electromagnetic signal. Similarly, the therapy electrodes can be configured to receive an electromagnetic signal.

Referring again to FIG. 3, the medical device controller 120 can further include an alarm module 326. It should be noted that the alarm module 326 can be part of the medical device controller 120 or a separate element of wearable therapeutic device 100. The alarm module 326 can be implemented using hardware, software, or a combination of hardware and software.

For instance, in some examples, the alarm module 326 can be implemented as a software component executed by the processor 318. Accordingly, instructions included in the alarm module 326 can cause the processor 318 to configure one or more alarm profiles (e.g., stored within the data storage 304) and notify intended recipients using the alarm profiles. For example, the alarm profiles stored in data storage 304 can include a list of alarm conditions (e.g., excessive noise above a predetermined threshold, electrode falloff event, among others), type of alarm or an alarm path (e.g., an audible or visual alert to the patient, a notification sent to a remote device or server, among others) and intended recipients of the alarm. In an example, the alarm module 326 can be an application-specific integrated circuit (ASIC) or a field-programmable gate array (FPGA) circuit coupled to the processor 318 and configured to manage alarm profiles in the data storage 304, and use the alarms specified within the alarm profiles to notify the intended recipients. An example alarm profile is summarized in the table below.

| Alarm condition | Alarm type or path | Recipient |
|---|---|---|
| Partial electrode falloff event (e.g., where only a portion of the sensing electrode has lost contact with the patient skin) | Audible alert to patient (e.g., a gong alert), visual alert (e.g., an animation indicating the electrode that has fallen off), and/or tactile alert indicating that the patient should adjust garment and/or electrode. The alert can also indicate which electrode of multiple electrodes needs attention. | Patient and/or other patient surrogate (e.g., a caregiver) Optionally, send notification to a remote entity (e.g., a technical support person or caregiver). |
| Electrode falloff event | Audible alert to patient (e.g., a gong alert), visual alert (e.g., an animation indicating the electrode that has fallen off), and/or tactile alert indicating that the patient should adjust garment and/or electrode. The alert can also indicate which electrode of multiple electrodes needs attention. | Patient and/or other patient surrogate (e.g., a caregiver) Send notification to a remote entity (e.g., a technical support person or caregiver). |
| Repeated partial falloff or complete falloff events | Upon exceeding a predetermined number of falloff event occurrences (e.g., 5 events within 2 hours), an audible or visual notification can be provided to the patient to contact a technical support person for further examination of the device. | Upon exceeding a predetermined number of falloff event occurrences within a period of time (e.g., 5 events within 2 hours), optionally, a notification can be sent to a predesignated remote entity (e.g., technical support or caregiver). |
| Multiple partial falloff or complete falloff events occurring substantially simultaneously (e.g., two or more electrodes afflicted by partial falloff or complete falloff events at substantially the same time) | Audible alert to patient (e.g., a gong alert), visual alert (e.g., an animation indicating the electrode that has fallen off), and/or tactile alert indicating that the patient should adjust garment and/or electrode and/or contact technical support or a caregiver for assistance. | Patient and/or other patient surrogate (e.g., a caregiver) Send notification to a remote entity (e.g., a technical support person or caregiver). |

In certain implementations, the alarm module 326 can be configured to provide various alerts such as audio alerts, visual alerts, tactile alerts, and a combination of two or more alerts. For example, the alarm module can be configured to provide alerts via speaker 230 and touchscreen 220 as described above in FIG. 2A, as well as tactile alarms via a tactile feedback device. In some examples, alarm module 326 can be configured to provide a notification that the sensing electrodes 112 or therapy electrodes 114 are improperly positioned or have fallen off, as determined by, for example, the electrode falloff detector 324. The alarm module 326 can also be configured to provide a notification that sensing electrodes 112 or therapy electrodes 114 are properly positioned. For example, the electrode falloff detector can be configured to provide a signal if no falloff events have been detected. In response to this signal, the alarm module can provide an indication (e.g., via the touchscreen 220) that the electrodes are properly positioned.

In the above example, the electrode falloff detector 324 can continually monitor the various electrodes to detect a falloff condition. The falloff detection process can be sequential in nature and includes stepping through each of the electrodes in turn to detect a falloff condition. The electrode falloff detection process can also include a scheme where all electrodes can be monitored at essentially the same time (e.g., as described below, various components and devices for detecting falloff can be provided locally at the individual electrodes, independent of the other electrodes to facilitate such an electrode falloff detection process).

It should be noted that the therapy electrodes 114 and the therapy delivery interface 302 as shown in FIG. 3 are optional components and are included to fully illustrate that the medical device controller can be designed and/or configured to function as a controller for both a therapeutic medical device as well as a monitoring medical device. For example, if the medical device controller 120 is designed to be used in a monitoring medical device, the therapy electrodes and the therapy delivery interface can be included as optional components. In certain implementations, a monitoring medical device can be converted to a therapeutic medical device by either adding (e.g., in a modular component) the therapy delivery interface and associated therapy electrodes, or by activating an existing therapy delivery interface, thereby converting a monitoring medical device to a therapeutic medical device. Conversely, the opposite can be true where a therapeutic medical device can be converted to a monitoring medical device can removing or deactivating the therapy delivery interface and associated therapy electrodes.

Temperature-Based Falloff Event Detection

Figure 4:
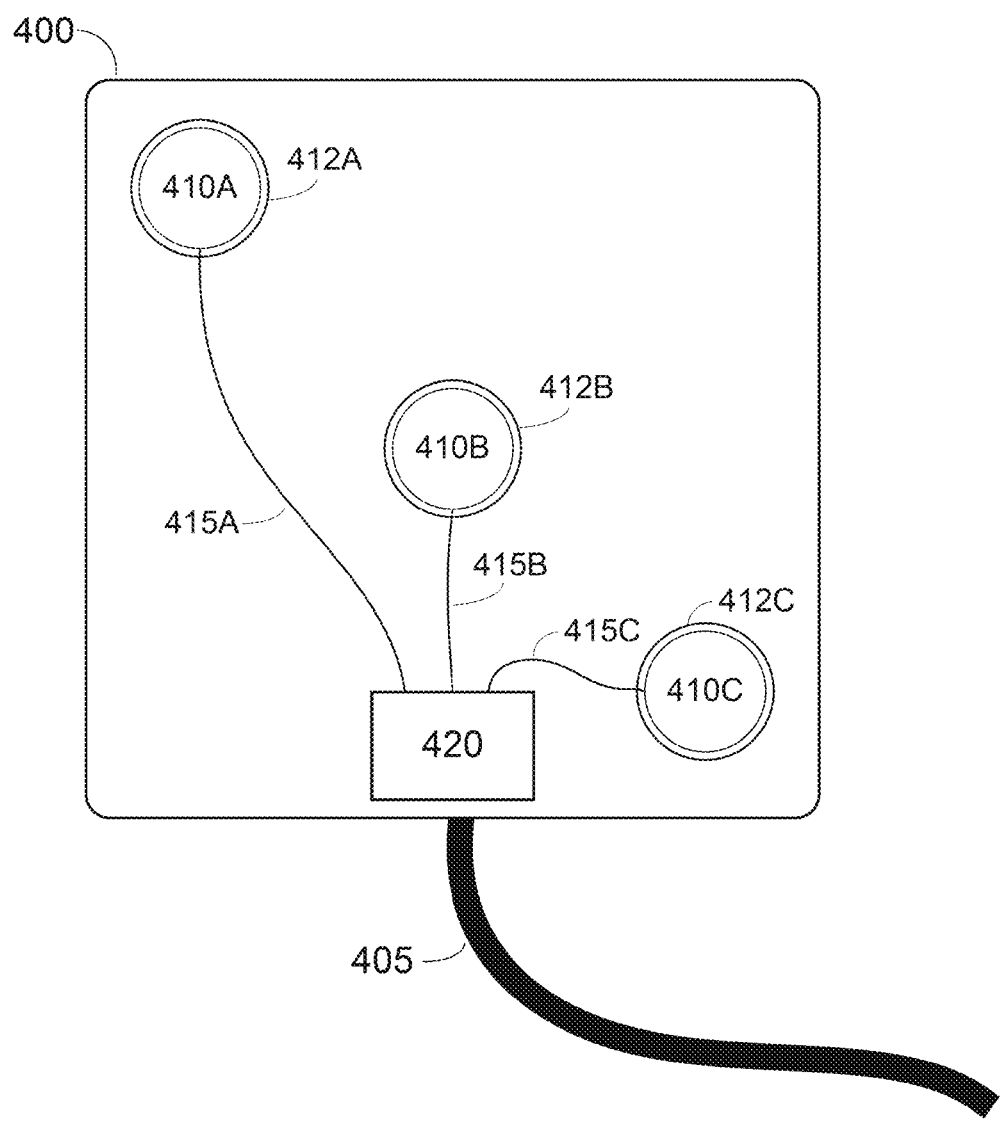
FIG. 4 depicts an electrode including one or more temperature sensors, in accordance with an example of the present disclosure.
Figure 5:
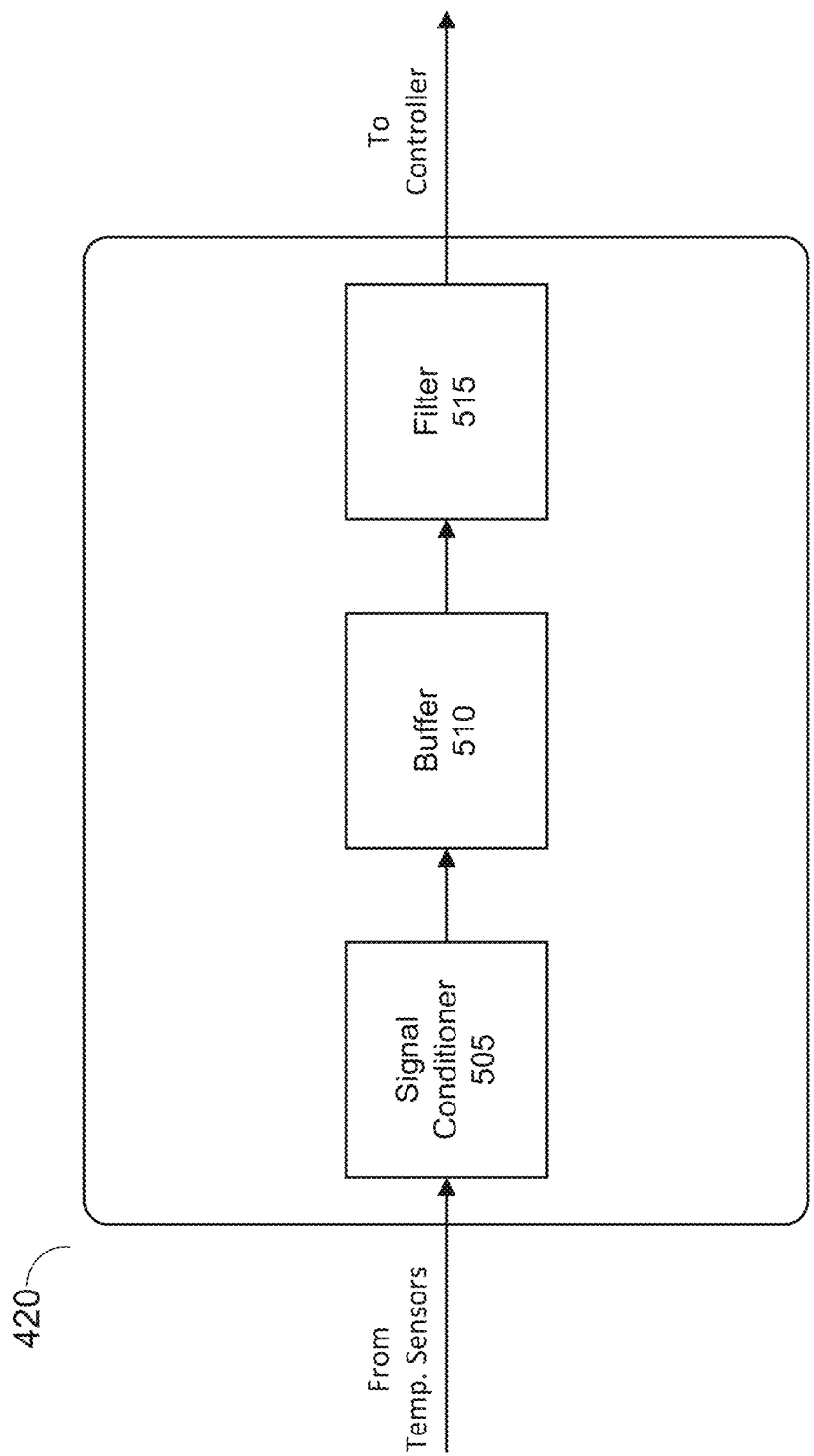
FIG. 5 depicts a sample processing circuit for an electrode having one or more temperature sensors, in accordance with an example of the present disclosure.
Figure 6:
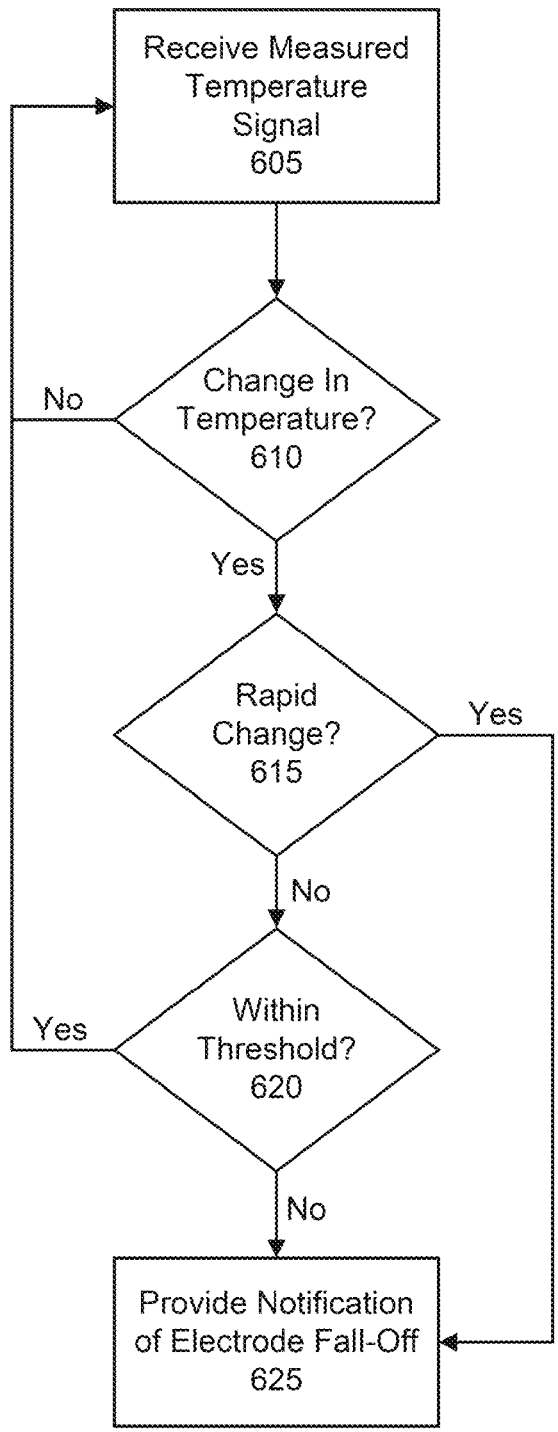
FIG. 6 depicts a process flow for determining a falloff event in an electrode having one or more temperature sensors, in accordance with an example of the present disclosure.

In an example, as illustrated in FIGS. 4-6, a temperature-based falloff detection scheme can be included in a wearable medical device. In such a scheme, one or more temperature sensors can be integrated into the electrodes. A processing circuit can also be implemented into the electrodes such that output from the temperature sensors can be processed (e.g., conditioned and filtered) prior to the medical device controller receiving the temperature sensor outputs for further processing. In such an example, the medical device controller can monitor the temperature sensor outputs for all the electrodes simultaneously (or, depending upon processing capabilities, substantially simultaneously) to detect an electrode falloff, e.g., when some or all of the conductive portion of the sensing electrode loses contact with the patient's skin. For example, the temperature sensor may provide an output signal for a specific electrode indicating a large and sudden temperature change (e.g., a 3-15° F. drop in temperature in 10-50 ms) in an interface between the electrode and the patient's skin. The temperature and corresponding time interval range provided above is intended as an illustration. Other temperature and time interval values can be used. Further, the amount of temperature change and corresponding time interval may be established by configurable parameters during initial device set up. The medical device controller can receive the signal including the temperature change information, process the information to determine that the sensor has likely fallen off, and provide a notification to a patient. For example, the notification may be provided to the patient as an audible, tactile, or visual alarm. For example, the controller can cause the medical device to display a message on a display device such as touch screen 220. The medical device controller can then instruct the patient to check the specific electrode and verify that the electrode is making proper connection with the patient's skin. The following discussion of FIGS. 4-6 provides additional details related to electrode falloff detection using temperature sensors.

FIG. 4 illustrates a sample electrode 400 that uses a temperature-based falloff detection process. It should be noted that, as shown in FIG. 4, the electrode 400 can be an electrode having at least one side configured to be placed against a patient's skin. For example, the electrode 400 can be either a sensing electrode or a therapy electrode as described above. The electrode 400 can be electrically coupled to a wire 405 configured to carry signals such as physiological signals (e.g., ECG signals and/or heart or lung sound signals) measured by the electrode 400 to another device such as connection pod 130 or controller 120 as described above in reference to FIG. 1. For explanatory purposes only, wire 405 as described herein can be configured to bi-directionally carry signals between the electrode 400 and a medical device controller.

The electrode 400 can include multiple temperature sensors 410A, 410B and 410C disposed on the electrode 400. Although three sensors are shown, any number of sensors may be used. Further, these sensors are shown as being placed along a diagonal of the electrode. Yet variations in locations of the sensors are possible. Further, the electrode itself may assume various shapes and as such the locations of the sensors may change accordingly. In certain implementations, each of temperature sensors 410A, 410B and 410C can be a thermocouple. A thermocouple is an electrical device typically including two different conductors arranged to form electrical junctions at differing temperatures. A thermocouple can be configured to produce a temperature-dependent voltage as a result of a thermocouple effect resulting between physical interactions between the two conductors as a result of temperature changes. This voltage can be measured and interpreted by an appropriate processing circuit to measure current temperature and temperature change over time. Thermocouples can be designed to be self-powered without any external excitation and, as such, can be packaged in a relatively small enclosure compared to other methods of temperature measurement such as a thermistor. However, it should be noted that additional temperature sensors such as thermistors, resistance temperature detectors, pyrometers, infrared temperature sensors, and other thermometers and temperature sensors can be used.

In certain implementations, depending upon the material used to make the conducting portion of the electrode 400, the electrode 400 can have a large thermal mass. In such an example, when the electrode loses contact with a patient's skin (i.e., there is a falloff event), the temperature of the electrode 400 can gradually decrease rather than drop quickly. As such, one or more of the temperature sensors 410A, 410B, 410C can be insulated from the material used to make the conducting portion of electrode 400. For example, as shown in FIG. 4, each temperature sensor 410A, 410B, 410C can be positioned such that it is insulated by insulating material 412A, 412B and 412C respectively. As shown in FIG. 4, each of insulating material 412A, 412B, 412C can be similarly shaped to the temperature sensors 410A, 410B, 410C. However, it should be noted that this shape is shown by way of example only, and additional shapes can be used for the insulating material 412A, 412B, 412C.

Based upon the size and design of electrode 400, various materials can be used for the insulating material 412A, 412B, 412C. For example, a thermoplastic foam such as polystyrene can be used for the insulating material 412A, 412B, 412C. Additional types of insulations such as aerogel, polyurethane, thermoset plastics, cellulose materials, and other similar insulations can be used for insulating material 412A, 412B, 412C depending on the size, shape, and design of electrode 400.

Referring again to FIG. 4, each temperature sensor 410A, 410B, 410C can be operably connected to a processing circuit 420. In certain implementations, temperature sensor 410A can be electrically coupled to the processing circuit 420 by connection 415A (e.g., a copper wire configured to transmit a signal produced by the temperature sensor 410A to the processing circuit 420), temperature sensor 410B can be electrically coupled to the processing circuit 420 by connection 415B, and temperature sensor 410C can be electrically coupled to the processing circuit 420 by connection 415C.

To continue the above example, each of temperature sensors 410A, 410B, 410C can be implemented as a thermocouple. In such an example, connections 415A, 415B, 415C can be copper (or another similarly conductive material) wires configured to carry an electrical signal generated by one or more of the thermocouples to the processing circuit 420. Processing circuit 420 can then further process the electrical signal generated by one or more of the thermocouples and transmit the processed signal through wire 405 to a medical device controller such as controller 120 as described above.

Depending upon the implementation of the electrode 400, the processing circuit 420 can be implemented in various manners. For example, the processing circuit 420 can be a standalone processing device configured to receive an analog signal from the temperature sensors 410A, 410B, 410C, condition and filter the signal to minimize noise and interference effects, and convert the analog signals to digital signals for transmission to a controller over the wire 405. In certain implementations, the processing circuit 420 can be implemented as a direct conversion analog-digital converter configured to generate a digital code for a specific voltage range received from the temperature sensors 410A, 410B, 410C. The processing circuit 420 can be configured to transmit the digital code over wire 405 to the medical device controller for further processing.

In a specific example, T-type thermocouple can be used for temperature sensors 410A, 410B, 410C. A T-type thermocouple includes a titanium lead and a copper/constantan lead. The two leads are joined at a junction. Based upon the material differences, as temperatures change at the junction, a voltage produced by the junction changes as well. For example, for a T-type thermocouple, at 98° F. (approximately 37° C.), an output voltage of approximately 1.5 mV can be output by the thermocouple. At 90° F., the output voltage drops to approximately 1.28 mV. By measuring the changes in output voltage from the thermocouples, the medical device controller (e.g., via the electrode falloff detector 324) can monitor for an electrode falloff event. The thermocouple may be selected based on its dynamic response to changes in sensed temperatures. Further, the temperatures described above as for illustration only. Other temperatures and corresponding voltages are possible.

As illustrated in FIG. 5, the processing circuit 420 can also include various circuit components for conditioning and filtering the signals received from the temperature sensors 410A, 410B, 410C prior to transmitting the signals to the medical device controller. For example, as shown in FIG. 5, a signal conditioner 505 can be configured to receive one or more signals from the temperature sensors, e.g., temperature sensors 410A, 410B, 410C. The signal conditioner 505 can be configured to convert the received signal into a format for transmission to and reading by, for example, the medical device controller. In certain implementations, the signal conditioner 505 can be implemented as an analog-to-digital converter configured to convert the analog signals received from the temperature sensors to a signal formatted for processing by the medical device controller. In some examples, the output of the signal conditioner 505 can be passed to a buffer 510. The buffer 510 can be configured to function as a voltage amplifier that functions to convert the output of the signal conditioner 505 to a signal tuned specifically for processing by the medical device controller. For example, the buffer 510 can be implemented as a voltage buffer amplifier configured to transfer the conditioned signals received from the signal conditioner 505 (received from, for example, a low impedance source such as temperature sensors 410A, 410B, 410C) to a high impendence level circuit such as the medical device controller. In some examples, the buffer 510 can be implemented as a unity gain buffer where the output signal of the buffer 510 has the same or essentially the same impedance as the input signal.

The output of the buffer 510 can be transferred to a filter 515 for filtering of the signal prior to transmission to the medical device controller. For example, the filter 515 can be a lowpass filter configured to preferentially attenuate frequencies below a cutoff frequency (e.g., 1 Hz) of the output of the buffer 510 for further processing by the medical device controller. In such an example, the filter 515 can be configured to smooth the temperature data obtained by the temperature sensors prior to transmitting the data to the medical device controller. In other implementations, the filter can be a highpass filter, a notch filter, or another similar filter familiar to those skilled in the art.

For example, the medical device controller can instruct the processing circuit (e.g., processing circuit 420) to sample the temperature information at a cutoff frequency of approximately 1 kHz (i.e., one temperature sample per millisecond). The output of the temperature sensors can be a voltage signal that changes in response to a measured voltage change by the sensors, but does not have an associated timing parameter. As such, the filter 515 can be configured to attenuate the sensor output signal to an appropriate 1 kHz signal for further processing by the medical device controller. However, it should be noted that a cutoff frequency of 1 kHz is provided by way of example only. Depending upon the operational parameters of the filter 515, and the processing capabilities of the medical device controller, the cutoff frequency can be set to various other values. For example, the medical device controller can set the cutoff frequency between 100 Hz and 2.5 kHz. Similarly, the medical device controller can set the cutoff frequency between 1 kHz and 100 kHz.

Referring again to FIG. 5, after the filter 515 attenuates the signal, the signal can be transmitted by the processing circuit to the medical device controller for further analysis to determine whether there has been any temperature change at the electrode that could indicate electrode falloff. For example, the processing circuit 420 can be configured to output the signal on a certain wire or channel in wire 405 for monitoring and analysis by the medical device controller. As noted above, in certain implementations an electrode falloff detector component such as electrode falloff detector 324 (as shown in FIG. 3 and described above) can be configured to monitor the output of the processing circuit 420 for any signal changes that could indicate one or more electrodes has fallen off the patient. A more detailed description of the functionality of an electrode falloff component is provided in the following description of FIG. 6.

It should be noted that the components as shown in FIG. 5 are provided by way of example only and, based upon the design of, for example, electrode 400 and processing circuit 420, one or more components can be removed from the design and one or more additional components can be added. For example, the processing circuit 420 can be implemented as a single integrated circuit configured to receive the output from the temperature sensors 410A, 410B, 410C, filter and attenuate the output, convert the output to a digital signal, and forward the digital signal for additional processing at, for example, the electrode falloff detector 324.

Additionally, one or more of the temperature sensors can be in thermal contact with the electrode 400, and the electrode falloff detection can be enhanced by measuring a temperature difference between a thermally insulated sensor (e.g., 410A, 410B, 410C as shown in FIG. 4) and at least one sensor that has a higher thermal conductivity with the electrode 400 as compared to the insulated sensors. The higher degree of thermal conductivity can be achieved by closer physical coupling between a sensor and the electrode 400 such as a machined groove in the electrode 400 in which the sensor is placed, or alternatively with a thermally conductive adhesive such as epoxy to adhere the sensor to the electrode. Because of the larger thermal mass of the electrode 400, the temperature readings of the thermally insulated sensors will equilibrate to ambient temperature with significantly shorter time constants than the temperature sensors with better thermal conductivity with the electrode. For example, in certain implementations, if the temperature difference exceeds 1 degree Celsius for more than 30 seconds, the electrode is determined to have fallen off.

FIG. 6 illustrates a sample process for monitoring one or more electrodes for a measured temperature change at the one or more electrodes that could indicate an electrode falloff. As noted above, a component such as an electrode falloff detector integrated in the medical device controller can be configured to monitor signals related to the various electrodes and determine whether one of the electrodes has fallen off the patient. However, it should be noted that this is for exemplary purposes only. Another component such as a multi-function processing device integrated into the medical device controller can be configured to monitor the electrodes for falloff events. As such, the following description including an electrode falloff detector is intended to provide a description of the process used to determine a falloff event rather than define what specific hardware component performs the process.

Referring to FIG. 6, the electrode falloff detector can be configured to receive 605 the temperature falloff signal from, for example, one or more of the electrodes. In certain implementations, each electrode can be operably connected to a node such as connection pod 130 as shown in FIG. 1. The node can include processing circuitry configured to concatenate, multiplex, or otherwise combine the temperature falloff signals from each of the electrodes into a single combined temperature falloff signal for transmission to the medical device controller. In such an example, the electrode falloff device can be configured to receive 605 the combined temperature falloff signal, divide the combined temperature falloff signal into individual components related to the individual electrodes, and process the individual components to determine whether one or more falloff events have occurred. Thus, in this example, the remainder of the process as shown in FIG. 6 can be repeated for each individual electrode that is associated with the combined temperature falloff signal.

In some implementations, each electrode can have a direct connection to the medical device controller. For example, the medical device controller can include one or more external connectors into which one or more electrodes can be directly connected. In such an example, the electrode falloff detector can be configured to receive 605 the temperature falloff signals directly from the individual electrodes. Thus, in this example, the entirety of the process as shown in FIG. 6 can be repeated for each electrode operably connected to the electrode falloff detector.

Referring again to FIG. 6, the electrode falloff detector can be further configured to determine 610 whether there has been a measurable temperature change at an electrode as indicated by the electrode's temperature falloff signal. If the electrode falloff detector determines 610 that there has not been a temperature change, the electrode falloff detector can receive 605 an updated temperature falloff signal.

Conversely, if the electrode falloff detector does determine 610 that there has been a temperature change, the electrode falloff detector can further determine 615 whether the temperature change was a rapid temperature change. Depending upon the programming and implementation of the electrode falloff detector, a particular time range and associated change in temperature can be used to label a temperature change as rapid. In certain implementations, if a temperature change of more than 10 degrees occurs in less than 1 second, the temperature change can be labeled as rapid. In some examples, if the temperature changes more than 5 degrees in less than 0.5 seconds, the temperature change can be labeled as rapid. For example, the electrode falloff detector can be configured to label a temperature change of 11 degrees that occurred in approximately 0.75 seconds as a rapid temperature change. The values discussed herein are for illustration only. Other temperature values and associated time values are possible. The electrode falloff detector can be configured to determine that a rapid change in temperature in a particular period of time is indicative of a falloff event. If such a determination is made, the electrode falloff detector can provide 625 a notification of a falloff event. Such a notification can be an instruction for an appropriate component of the medical device controller to issue an alarm of other similar notification to a patient or caregiver that one or more electrodes have fallen off. For example, the medical device controller can display a visual notification on a user interface such as touchscreen 220 (as described above in reference to FIG. 2A) to check a specific electrode for a potential falloff event. Depending upon the capabilities and the programming of the medical device controller, the visual notification can be accompanied by an audio alarm or some form of tactile feedback.

If the electrode falloff detector determines 615 that the temperature change was not a rapid change, the electrode falloff detector can be further configured to determine 620 whether the temperature change was within an allowed threshold. Based upon various measured patient parameters and/or operating parameters of the medical device controller and the electrode falloff detector, a certain threshold of temperature change can be determined as acceptable. In certain implementations, the medical device controller can include a baseline temperature for the patient. The acceptable threshold can be set as plus or minus a certain number of degrees from the baseline temperature. For example, the acceptable threshold can be set as plus or minus 2.5° F. for a particular patient. If the electrode falloff detector determines 620 that a temperature change at an electrode falls within the acceptable threshold, the electrode falloff detector can receive 605 an updated temperature falloff signal and repeat the process as shown in FIG. 6. Conversely, if the electrode falloff detector determines 620 that the temperature change is not within an acceptable threshold, the electrode falloff detector can provide 625 a notification of a potential falloff event.

In certain implementations, the electrode falloff detector can provide 625 an alarm to the patient indicating a potential falloff event. For example, the alarm can include a visual alarm, an audio alarm, a tactile alarm, a combination of alarms (e.g., alarms that are in a predefined sequence or that overlap, such as, first, initiating a tactile alert, second, initiating an audible alert, and third, initiating a visual alert on the display, or another similar alarm configured to provide an indication or notification of the potential falloff event to the patient wearing the medical device. In certain implementations, an alarm manager (e.g., alarm module 326 as described above) can be configured to output one or more alarms in response to a specific event occurring. For example, if a treatable cardiac event is detected, the alarm manager can be configured to cause a high volume audible alarm to occur. In some examples, a high volume audible alarm can be about 80 db as measured 1 meter from the output device (e.g., a speaker or audio resonator). In the event of an electrode falloff detection, the alarm manager can be configured to output a lower volume alarm. For example, the alarm manager can be configured to output an alarm about 6-12 db lower than the high volume alarm (e.g., an alarm ranging from 68-74 db). In some examples, the alarm manager can be configured to output a visual alarm. For example, the alarm manager can flash a message or notification on the medical device's screen (e.g., touchscreen 220 as described above) or another similar visual output device such as one or more LED outputs. In certain implementations, the alarm manager can be configured to provide a tactile alarm as a standalone alarm or in combination with one or more of the audio and visual alarms.

In addition to providing the patient notification of the potential electrode falloff, the electrode falloff detector can further provide 625 a notification to a remote server or monitoring service of the potential falloff. For example, the wearable medical device can be operably connected to a remote server (e.g., remote server 322 as described above) and can be configured to regularly transmit data indicative of a patient's cardiac activity as well as any detected events that occur while the patient is wearing the medical device. Upon detection of a potential electrode falloff, the electrode falloff detector can provide 625 a notification such as a time/date stamp and an associated flag indicative of the potential falloff event. Upon review of the patient's information (e.g., by a technician or a patient's physician) collected by the remote server, the potential falloff event can be reviewed as well. In certain implementations, a high amount of falloff events (e.g., more than 5 every 2 hours) can be indicative that the patient needs to have their wearable medical device adjusted or replaced.

In an example of the process as shown in FIG. 6, the electrode falloff detector can determine that, over a series of signals representing 30 seconds in time, a patient's temperature at a specific electrode has dropped 0.75° F. As this temperature drop falls within a 2.5° F. threshold, the electrode falloff detector can determine that there has not been a falloff event. To provide higher accuracy of whether a falloff event has occurred, the electrode falloff detector can compare measurements from multiple electrodes. For example, if a small temperature drop (e.g., 0.5° F.) is consistently measured across multiple electrodes, the electrode falloff detector can label the temperature change as a change in patient's body temperature rather than a falloff event. Such labels can be recorded in memory as flags, temperature events, or other similar events for review later by, for example, a technician or other person (such as a physician) reviewing patient-related information recorded by the wearable medical device.

It should be noted that the thresholds used for temperature-based falloff detection can be determined individually for each patient using the wearable medical device. For example, a patient can participate in a baselining process including measuring the patient's temperature during, for example, a garment fitting for the wearable medical device when the patient is first subscribed the device. Additionally, the patient can be instructed to perform a physical activity such as a six-minute walk test to measure how the patient's body temperature changes during physical activity. In such an example, the thresholds can be dynamically alterable for a patient depending upon whether the patient is engaged in physical activity. Additional information such as accelerometer information can also be measured during the physical activity to determine what measurable parameters and characteristics as associated with the patient during physical activity.

Additionally, an electrode can include a temperature sensor for measuring an ambient temperature around the electrode. For example, as shown in FIG. 4, temperature sensors 410A and 410C can be positioned such that they contact the patient's skin. Temperature sensor 410B can be positioned on an electrode surface away from the patient's skin, and can be configured to measure an ambient temperature around the electrode. The ambient temperature information can be used to determine how accurate and reliable a temperature-based falloff scheme is for a given environment and situation. For example, if a patient is outside on a summer day and the ambient air temperature is around 95° F., the medical device controller can determine that the temperature-based falloff scheme is not likely to produce reliable information as a falloff event could result in a 3° F. change. Such a change could be within the acceptable threshold and, as such, not register properly as a falloff event. In such an example, the temperature-based falloff detection scheme can be used in concert with another detection scheme as described herein.

As noted above, additional temperature sensors such as thermistors, resistance temperature detectors, pyrometers, infrared temperature sensors, and other thermometers and temperature sensors can be used for temperature sensors 410A, 410B, 410C. Each such sensor could be implemented in the electrodes in a similar manner. For example, the temperature sensors 410A, 410B, and 410C can be implemented as resistance temperature sensors. A small current (e.g., 5 mA) can be passed through the resistance temperature sensors. As the temperature around the resistance temperature sensors changes, the resistance of the resistance temperature sensors changes in a linear manner. As such, by measuring the voltage change across the resistance temperature sensor, the processing circuit 420 can determine a temperature falloff signal for further analysis by the electrode falloff detector.

Capacitance-Based Falloff Event Detection

In another example, as illustrated in FIGS. 7-15, a capacitance-based falloff detection scheme can be included in a wearable medical device. In such a scheme, one or more capacitance or touch sensors can be integrated into the electrodes. A processing circuit can also be implemented into the electrodes such that output from the capacitance sensors can be processed (e.g., conditioned and filtered) prior to the medical device controller receiving the capacitance sensor outputs for further processing. In such an example, the medical device controller can monitor the capacitance sensor outputs for all the electrodes simultaneously (or, depending upon processing capabilities, substantially simultaneously) to detect an electrode falloff, e.g., when some or all of the conductive portion of the sensing electrode loses contact with the patient's skin. For example, the capacitance sensors can be configured to receive an input capacitance form a patient's body through contact between the patient's skin and the capacitance sensor mounted in an electrode. The capacitance sensors can continually measure the patient's capacitance and transmit the information to a processing circuit, which can then transmit the information to the medical device controller. The medical device controller, or a component of the medical device controller such as the electrode falloff detector, can receive a capacitive falloff signal including the capacitance change information, process the information to determine that the sensor has likely fallen off, and provide a notification to a patient (e.g., via an alarm or by displaying a message on a display device such as touch screen 220 as described above) that the sensor has likely fallen off. The medical device controller can then instruct the patient to check the specific electrode and verify that the electrode is making proper connection with the patient's skin. The following discussion of FIGS. 7-15 provides additional details related to electrode falloff detection using capacitance sensors.

In certain implementations, a capacitor-based falloff detection scheme can be implemented as an oscillation-based system configured to measure changes in frequency induced by skin contact such as a "Theremin" configuration known to those skilled in the art. The oscillation frequency can be related to a frequency that results from measuring a patient's electrical characteristics including a measured frequency. In certain implementations, the measured frequency can be between 200 Hz and 20 kHz. By measuring a change in this frequency (as a result of the electrode losing contact with the patient's skin), a falloff event can be detected.

Figure 7:
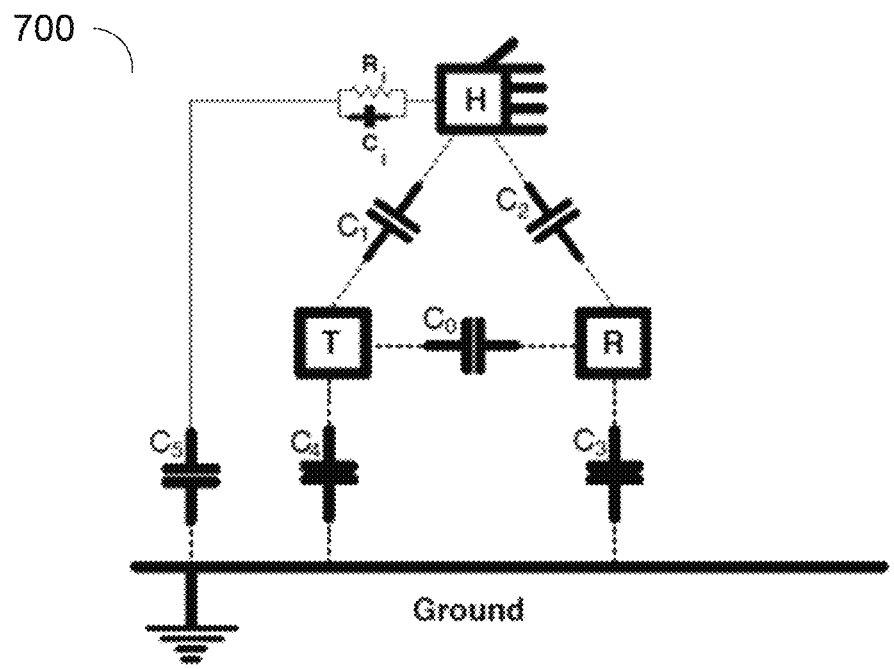
FIG. 7 depicts a lumped circuit model for electric field sensing, in accordance with an example of the present disclosure.

FIG. 7 illustrates a lumped circuit model 700 for electric field sensing that can be integrated into a capacitive electrode for use in detecting electrode falloff. The general term electric field sensing encompasses several different measurements, which correspond to different current pathways through this diagram. In sensing mode, a low frequency (e.g., 10-100 kHz) voltage signal is applied to the transmit electrode, labeled T in FIG. 7. A displacement current can flow from the transmitter to the other conductors through the effective capacitors shown in circuit model 700. In loading mode, the current flowing from the transmitter can be measured. The value of C1, and thus the load on the transmitter, can change with hand position. For example, when the hand, labeled H in FIG. 7, moves closer to the transmitter, the loading current increases.

The term capacitive sensing ordinarily refers to a loading mode measurement. However, the capacitances other than C1 in FIG. 7 can provide for other measurements. In transmit mode, when the transmitter is coupled strongly to the body—C1 is very large— so the hand is essentially at the potential of the transmitter. As the body approaches the receive electrode, labeled R in FIG. 7, the value of C2 (and C0—the two are not distinct in this mode) increases, and the displacement current received at R increases. In shunt mode, C0, C1, and C2 can be of the same order of magnitude. As the hand approaches the transmitter and receiver, C1 increases and C0 decreases, leading to a drop in received current. As such, the displacement current that had been following to the receiver is shunted by the hand to ground (hence the term shunt mode). A baseline received current can be measured when the hand is at infinity, and then subtract later readings from this baseline. With N ordinary capacitive sensors (loading mode), N numbers can be collected. These N numbers represent the diagonal of the capacitance matrix for the system of electrodes. In shunt mode, the N(N−1) off-diagonal elements can be measured. Because the capacitance matrix is symmetrical, there are ideally only ½(N−1) distinct values. In practice, measured deviations from symmetry provide valuable calibration information."

Figure 8:
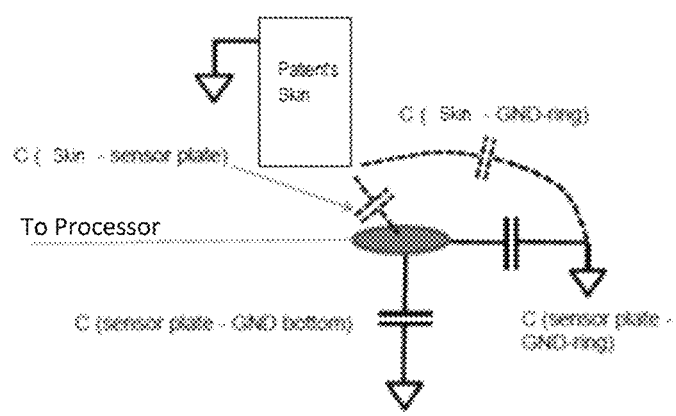
FIG. 8 depicts a circuit diagram representing the interaction between a patient's body part and an electric field sensor, in accordance with an example of the present disclosure.

In one implementation, the transmit and receive electrodes (labeled "T" and "R" in FIG. 7) are integrated into a capacitive electrode such as capacitive electrode 1200 described below in the discussion of FIG. 12. In some examples, a capacitive touch/proximity sensor circuit, such as the PCF8883 sensor circuit manufactured by NXP Semiconductors (Eindhoven Netherlands) can be used. The steady state capacitance between the sensor plates, traces, and GND can be compensated for by the auto-calibration mechanism built into the PCF8883 chip. Therefore, the primary condition to consider for design of sensor plates is to maximize the capacitance between an approaching portion of the patient's body (e.g., a portion of skin on the patient's chest or back) and the sensor plate. Likewise, the capacitance between the patient's skin and any GND can be minimized. As shown in FIG. 8, a ground ring can be provided to minimize stray field effects. The sensor plate size is per definition a major element in the sensitivity as it is defining the size of the parallel plate capacitor and the touching skin. In certain implementations, round-shaped sensor plates will provide a maximized sensing area.

A touch sensor such as the PCF8883 can be used react on certain changes in capacitance instead of measuring absolute capacitance. In certain implementations, provided the capacitive load is in the specified range of 10 pF to 40 pF, any capacitance changes occur and are measured at the speed of the electrode being removed from the body can be detected. The steady state capacitance originating from the layout, slowly changing environmental conditions, accumulating dirt, and so on, can be compensated for by the auto-calibration mechanism. Thus, the falloff detection can have a threshold related to at least one of the following parameters: 1) absolute capacitance level; 2) rate of capacitance change (e.g. change in Farads per second); 3) the amount of time required for the capacitance to exceed a particular capacitance level (the change might be instantaneous or averaged). The falloff detection threshold can be adjustable based on a particular patient characteristic such as weight, skin dryness, or the baseline electrical characteristics of the skin.

Figure 9:
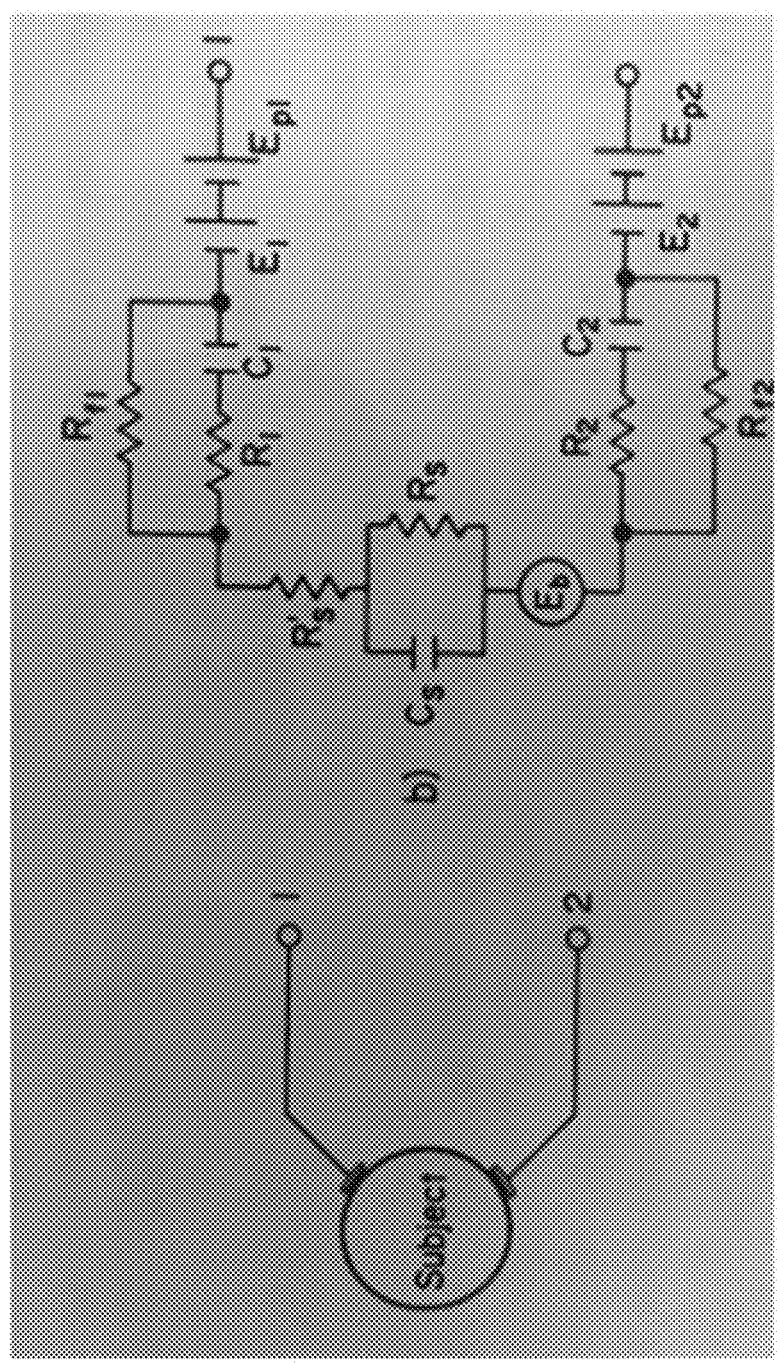
FIG. 9 depicts an electrode/skin model, in accordance with an example of the present disclosure.
Figure 10:
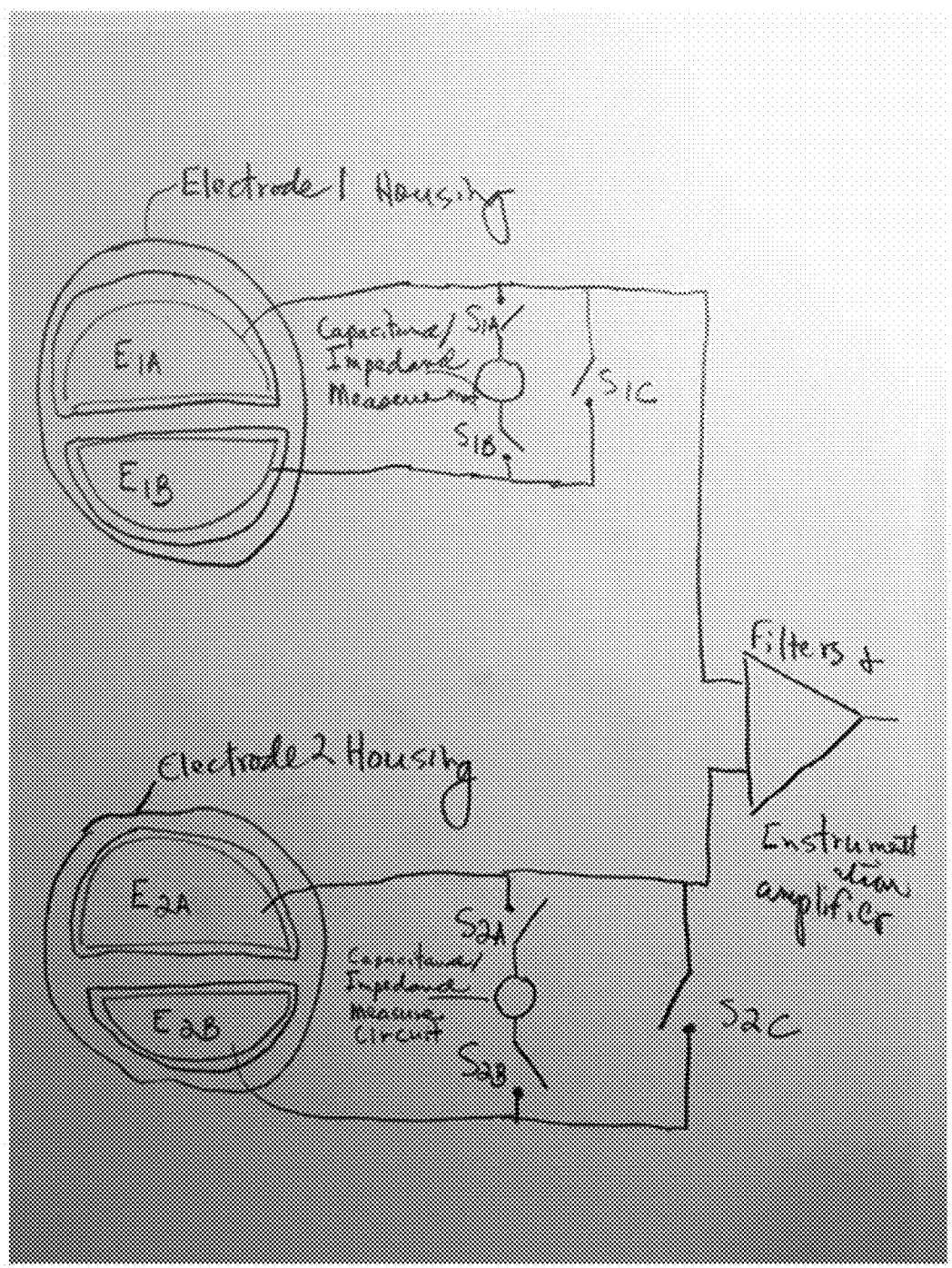
FIG. 10 depicts a split electrode model, in accordance with an example of the present disclosure.

In some implementations, the capacitive electrode can include a tantalum pentoxide coating, known to those skilled in the art. This coating can result in typical capacitance values of 200-900 nF measured at 1 kHz, with an ESR of 2-10K at 10 Hz. Referring to FIGS. 9 and 10, in some implementations, the electrode can be split into two or more electrical elements (e.g. $E_{1A}/E_{1B}$ and $E_{2A}/E_{2B}$) housed in the same electrode, as shown in FIG. 10 below. The two (or more) split elements of the electrode can be disposed in an electrically isolating housing made, for instance, from a plastic such as PET, polycarbonate, or another similar electrically isolating plastic. The electrode/skin contact can be modeled as a simple capacitance, or, as shown FIG. 9 (and explained in greater detail in the discussion of FIG. 19 below) as two or more of a combination of inductors, resistors or capacitors. In FIG. 9, by way of example, the electrode/skin interface can be modeled as a resistor and capacitor in series (e.g. $R_1C_1$, and $R_2C_2$) in parallel with another resistor (e.g. $R_{f1}$ or $R_{f2}$). Referring to FIGS. 10 and 11A-F, the capacitance or impedance measurement circuit may be located within the electrode housing, the cable connecting the electrode to the defibrillator, or in the defibrillator itself Locating the impedance measurement circuit at or near the distal end of the cable or within the electrode housing can act to lower any effects of stray impedance in the cable and thus obtain a more accurate capacitance/impedance measurement. Switch networks (e.g. $S1_{A\text{-}C}$, $S2_{A\text{-}C}$ as shown in FIG. 10) can be provided to switch the capacitance/impedance circuitry out of the ECG sensing circuitry to improve signal integrity. For example, switches $S1_C$ and $S2_C$ can be open and switches $S1_{A,B}$, $S2_{A,B}$ can be closed when measuring capacitance/impedance to electrically disconnect $E1_A$ from $E1_B$ from each other during capacitance/impedance measurement. Switches $S1_C$ and $S2_C$ will be closed and switches $S1_{A,B}$, $S2_{A,B}$ are open when monitoring the ECG to electrically connect $E1_A$ from $E1_B$ from each other disconnect from the capacitance/impedance measurement circuitry.

Referring to FIGS. 11A-F, the capacitance/impedance measurement circuitry can take a number of different configurations, known to those skilled in the art. For instance, the measurement circuit may employ the bridge method, resonant method, I-V method, RF-I-V method, network analysis method, or auto-balancing bridge method.

Figure 11A:
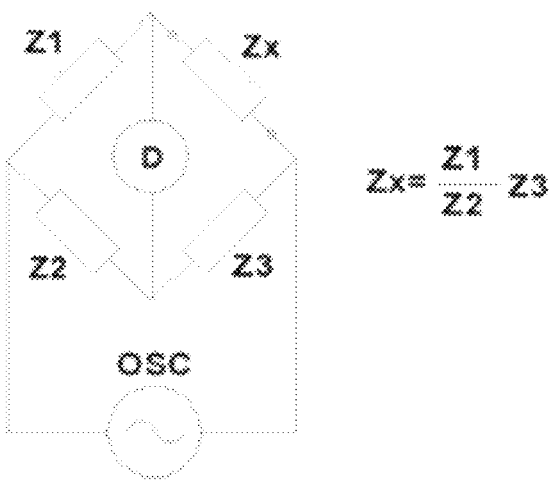
FIGS. 11A-F depict various examples of capacitance and/or impedance detection circuits, in accordance with an example of the present disclosure.

FIG. 11A illustrates a bridge implementation of a capacitance/impedance measurement circuit. When no current is flowing through the detector D, the value of the unknown impedance Zx can be determined based upon a known relationship of the other bridge elements. For example, as noted in FIG. 11A, $Zx=(Z1/Z2)*Z3$.

Figure 11B:
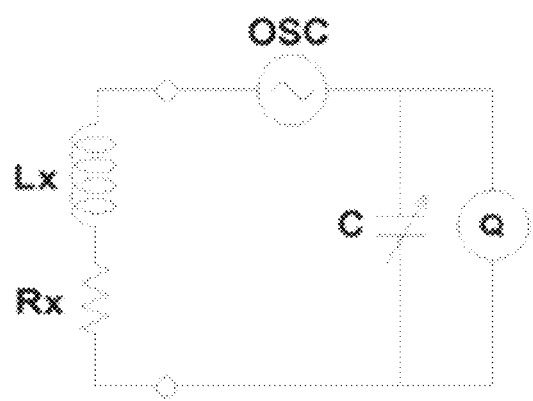

FIG. 11B illustrates a resonant method implementation of a capacitance/impedance measurement circuit. When the circuit is adjusted to resonance by tuning capacitor C, the unknown impedance values Lx and Rx are obtained from a test frequency, the value of C and the value of Q. Q can be measured directly using a voltmeter or another voltage measuring device. In addition to the direct connection shown in FIG. 11B, series and parallel connections can be used as well.

Figure 11C:
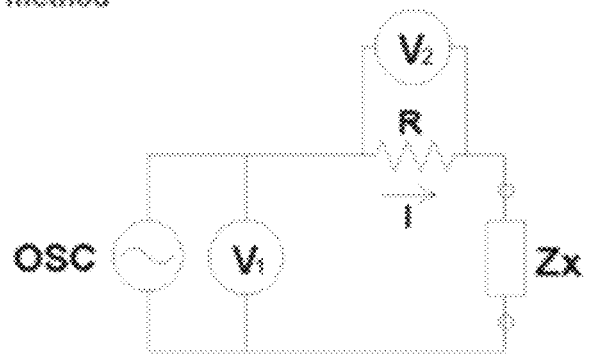

FIG. 11C illustrates an I-V method implementation of a capacitance/impedance measurement circuit. In this example, the unknown impedance Zx can be calculated from measured voltage and current values. The current can be calculated using the voltage measurement across a known resistor R. In practice, a low loss transformer can be used in place of R to prevent any circuit-wide effects of using a resistor. The transformer, however, can limit the low end of an applicable frequency range.

Figure 11D:
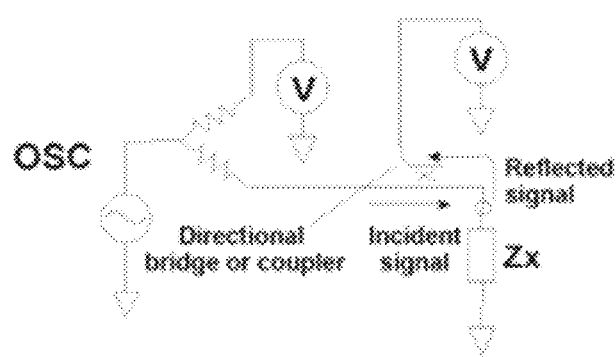

FIG. 11D illustrates a network analysis method implementation of a capacitance/impedance measurement circuit. In this example, a directional coupler or bridge can be used to detect a reflected signal and a network analyzer can be used to supply and measure the reflected signal and an incident signal.

Figure 11F:
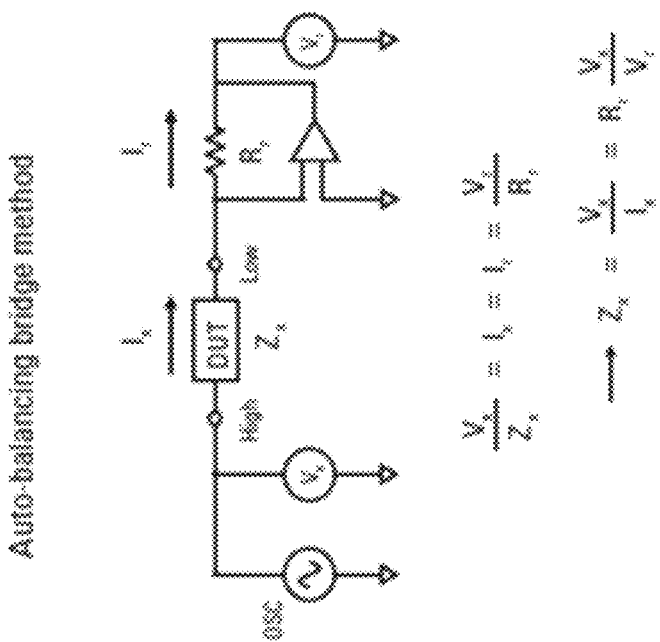
Figure 11E:
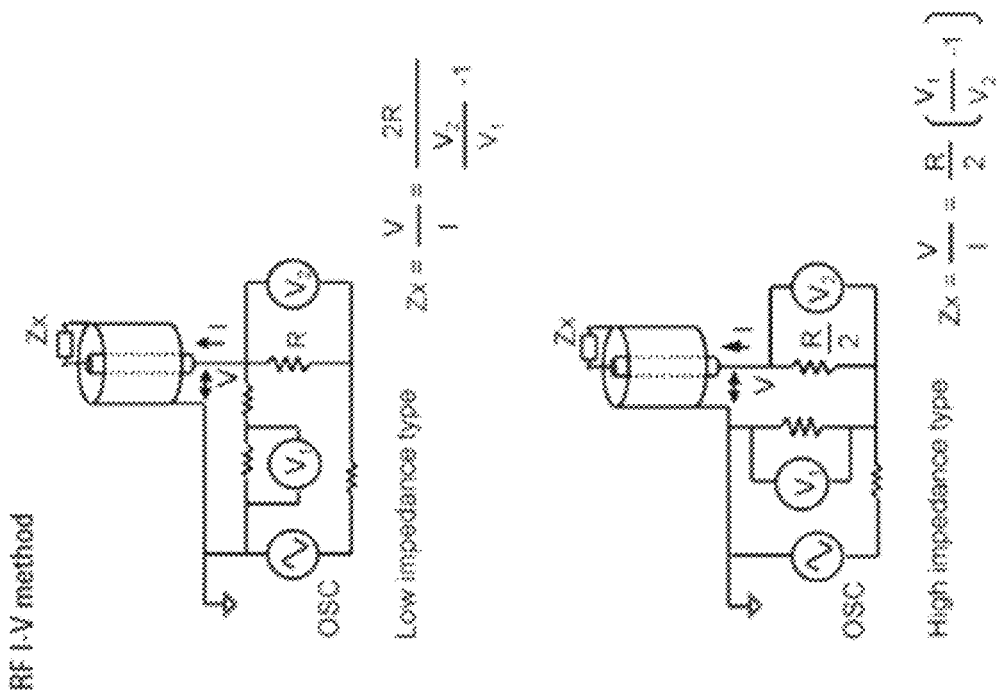

FIG. 11E illustrates an RF I-V method implementation of a capacitance/impedance measurement circuit. Both a low impedance circuit and a high impedance circuit are shown in FIG. 11E. While RF I-V measurement is based upon the same principles of the I-V measurement as shown in FIG. 11C, the RF I-V method can include an impedance matched measurement circuit (e.g., at 50Ω) and a precision test port for operation at higher frequencies.

FIG. 11F illustrates an auto-balancing bridge method implementation of a capacitance/impedance measurement circuit. In this example, the current Ix can balance with the current Ir which flows through the range resistor Rr. The potential at the Low point of the circuit can be maintained at zero volts, providing a virtual ground. The impedance of DUT can be calculated using the voltage measured at the High terminal (Vx) and across Rr (Vr).

It should be noted that the circuits provided in FIGS. 11A-F are provided by way of example only, and additional circuit implementations can be used for a capacitance/impedance measurement circuit.

Figure 12:
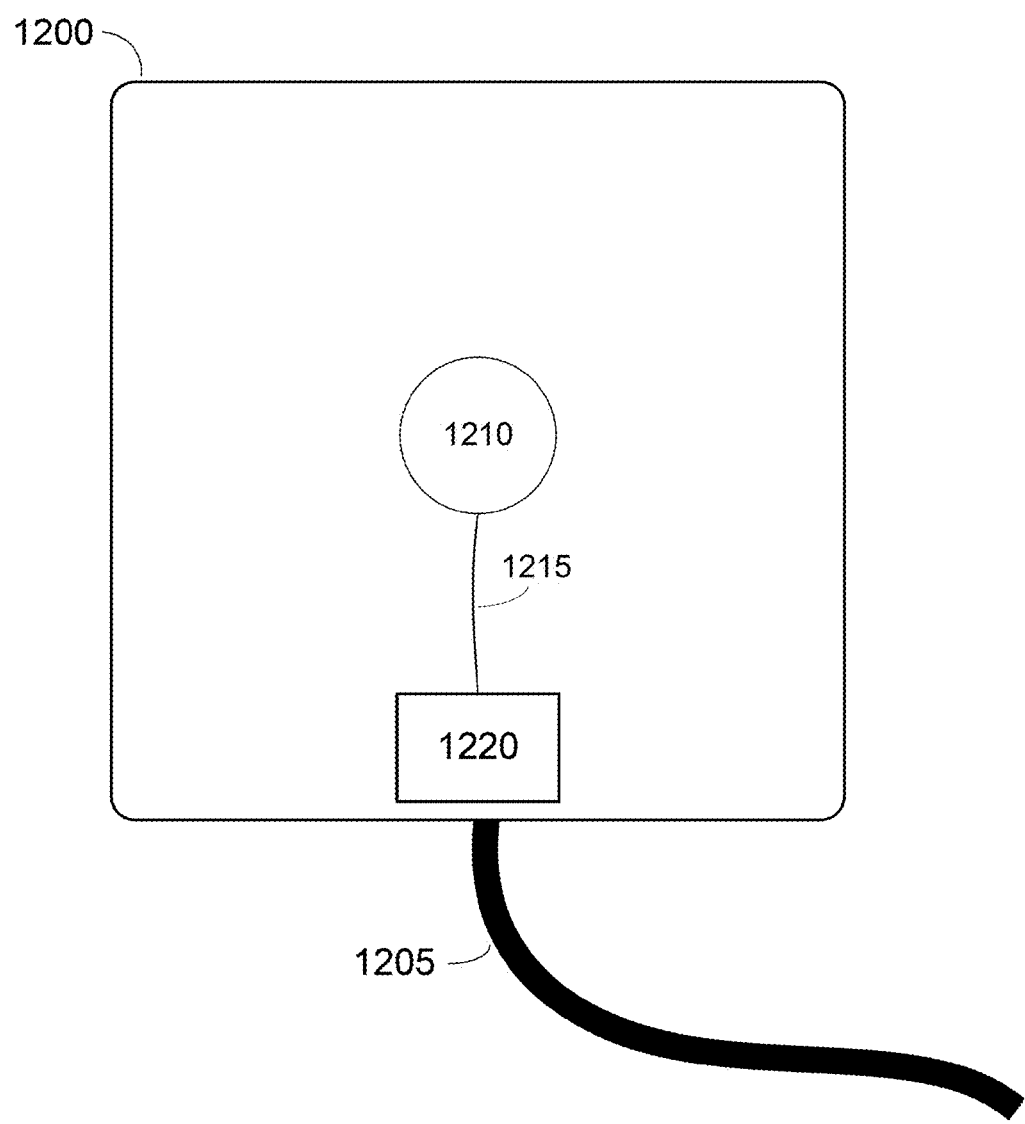
FIG. 12 depicts an electrode including one or more capacitive sensors, in accordance with an example of the present disclosure.

FIG. 12 illustrates a sample electrode 1200 that uses a capacitance-based falloff detection process. It should be noted that, as shown in FIG. 12, the electrode 1200 can be an electrode having at least one side configured to be placed against a patient's skin. For example, the electrode 1200 can be either a sensing electrode or a therapy electrode as described above. The electrode 1200 can be electrically coupled to a wire 1205 configured to carry signals such as physiological signals measured by the electrode 1200 to another device such as connection pod 130 or controller 120 as described above in reference to FIG. 1. For explanatory purposes only, wire 1205 as described herein can be configured to bi-directionally carry signals between the electrode 1200 and a medical device controller.

The electrode 1200 can include, for example, capacitive sensor 1210. In certain implementations, the capacitive sensor 1210 can be a dielectric-sensing capacitive sensor configured to measure dielectric values for materials in contact with the sensor. A capacitive sensor such as capacitive sensor 1210 can be constructed to have at least one side that is coated with a conductive material such as copper, Indium Tin oxide, a conductive ink, and other similar conductive coatings. A voltage is applied to the conductive side, resulting in a uniform electrostatic field. When a conductive object, such a patient's skin, touches the uncoated side of the electrode, a capacitive interface is formed. Because of resistance inherent in the material used to make the capacitive sensor, each point about the periphery has a different effective capacitance. A controller can measure the effective capacitances at various points about the periphery of the capacitive sensor to determine the location of contact between the capacitive sensor the patient's skin. Additionally, a value indicative of the amount of surface area of the capacitive sensor in contact with the patient's skin can be determined as well.

Referring again to FIG. 12, the capacitive sensor 1210 can be operably connected to a processing circuit 1220 by connection 1215. In such an example, connection 1215 can be a copper (or another similarly conductive material) wire configured to carry an electrical signal generated by the capacitive sensor 1210 to the processing circuit 1220. Processing circuit 1220 can then further process the electrical signal generated by the capacitive sensor 1210 and transmit the processed signal through wire 1205 to a medical device controller such as controller 120 as described above.

Depending upon the implementation of the electrode 1200, the processing circuit 1220 can be implemented in various manners. For example, the processing circuit 1220 can be a standalone processing device or integrated circuit configured to receive an analog signal from the capacitive sensor 1210 and convert the analog signal to a digital signal for transmission to a controller over the wire 1205. In certain implementations, the processing circuit 1220 can be implemented as a direct conversion analog-digital converter configured to generate a digital code for a specific voltage range received from the capacitive sensor 1210. The processing circuit 1220 can be configured to transmit the digital code over wire 1205 to the medical device controller for further processing.

In a specific example, a dielectric-sensing capacitive sensor can be used to measure a dielectric value at each electrode. A dielectric-sensing capacitive sensor can use capacitive coupling (i.e., the transfer of energy between two objects) to detect and measure a dielectric value for anything having a different dielectric than air. For example, human skin has a dielectric value of approximately 0.1 S/m (Siemens per meter) at a 100 Hz sampling rate. In the event of a falloff event, the measured dielectric value at a dielectric-sensing capacitive sensor would drop to zero. By measuring the changes in measured dielectric values output by the capacitive sensor, the medical device controller (e.g., via the electrode falloff detector 324) can monitor for an electrode falloff event.

Figure 13:
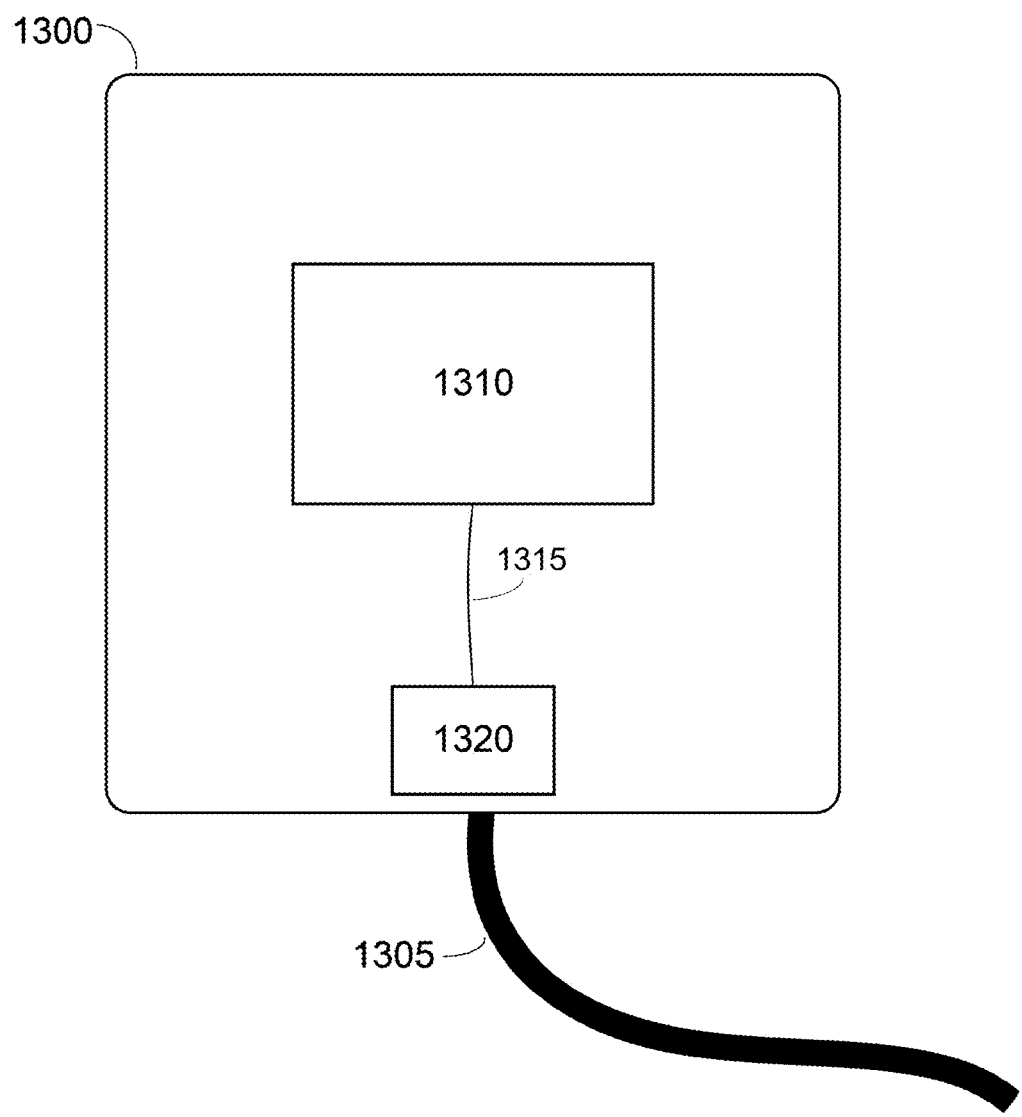
FIG. 13 depicts an electrode including one or more touch sensors, in accordance with an example of the present disclosure.

Additional types of capacitive sensors can also be used to detect electrode falloff events. For example, FIG. 13 illustrates a sample electrode 1300 that uses a capacitive touch panel for implementing the falloff detection process. The electrode 1300 can be electrically coupled to a wire 1305 configured to carry signals such as physiological signals measured by the electrode 1300 to another device such as connection pod 130 or controller 120 as described above in reference to FIG. 1. For explanatory purposes only, wire 1305 as described herein can be configured to bi-directionally carry signals between the electrode 1300 and a medical device controller.

The electrode 1300 can include, for example, capacitive touch panel 1310. In certain implementations, the capacitive touch panel 1310 can be an electrostatic-based touch panel. The capacitive touch panel 1310 can be operably connected to a processing circuit 1320 by connection 1315. In such an example, connection 1315 can be a copper (or another similarly conductive material) wire configured to carry an electrical signal generated by the capacitive touch panel 1310 to the processing circuit 1320. Processing circuit 1320 can then further process the electrical signal generated by the capacitive touch panel 1310 and transmit the processed signal through wire 1305 to a medical device controller such as controller 120 as described above.

Depending upon the implementation of the electrode 1300, the processing circuit 1320 can be implemented in various manners. For example, the processing circuit 1320 can be a standalone processing device configured to receive an analog signal from the capacitive touch panel 1310 and convert the analog signal to a digital signal for transmission to a controller over the wire 1305. In certain implementations, the processing circuit 1320 can be implemented as a direct conversion analog-digital converter configured to generate a digital code for a specific voltage range received from the capacitive touch panel 1310. The processing circuit 1320 can be configured to transmit the digital code over wire 1305 to the medical device controller for further processing.

As noted above, in a specific example, an electrostatic-based touch panel can be used to monitor contact between a patient's skin and the electrode. An electrostatic-based touch panel typically includes an insulator such as glass coated with a transparent conductor (such as Indium Tin oxide). As human skin touches the surface of the panel, the contact distorts the panel's electrostatic field, which is measurable in a change in capacitance of the panel. Additionally, by using location-determining technologies such as triangulation using multiple electrostatic fields, locational information related to the contact point on the panel can be determined. Similarly, the electrostatic-based touch panel can use multi-touch technology to detect multiple contact points at various locations about the panel. By measuring the changes in measured capacitance values output by the capacitive touch panel (at one or more locations on the panel), the medical device controller (e.g., via the electrode falloff detector 324) can monitor for an electrode falloff event. Additionally, if the capacitive touch panel is configured to measure contact at multiple locations, a quantitative analysis of how much surface area of the electrode is touching the patient's skin can be determined. In such an example, even if a falloff event has not occurred, a patient can be instructed to reposition the electrode such that there is better overall contact against their skin.

Figure 14B:
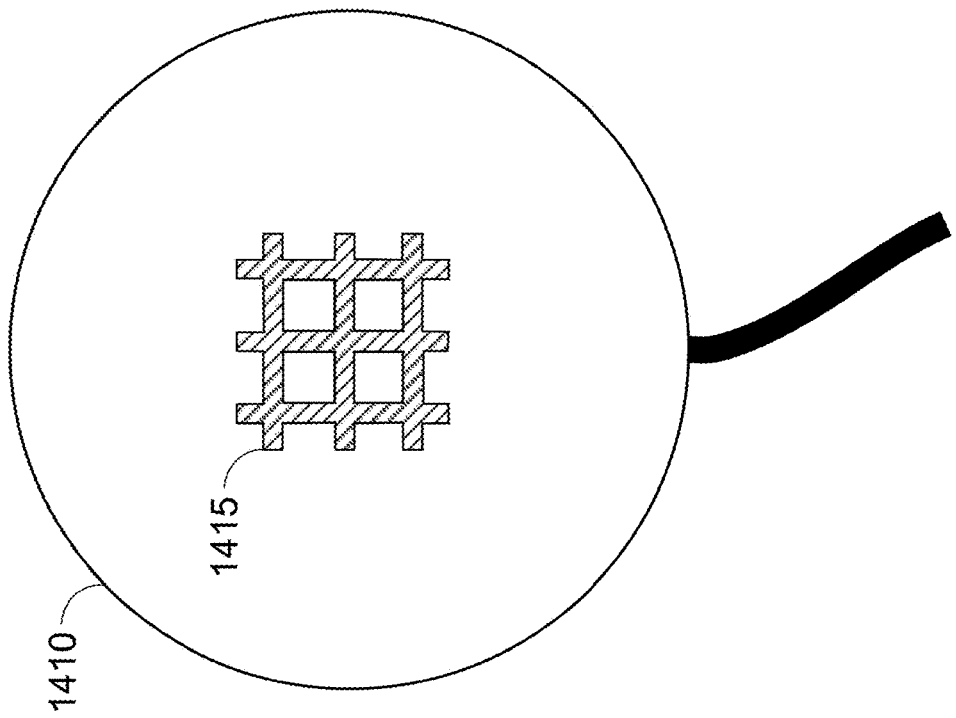
FIGS. 14A and 14B depict an electrode including various configurations of electric-field proximity sensors, in accordance with an example of the present disclosure.
Figure 14A:
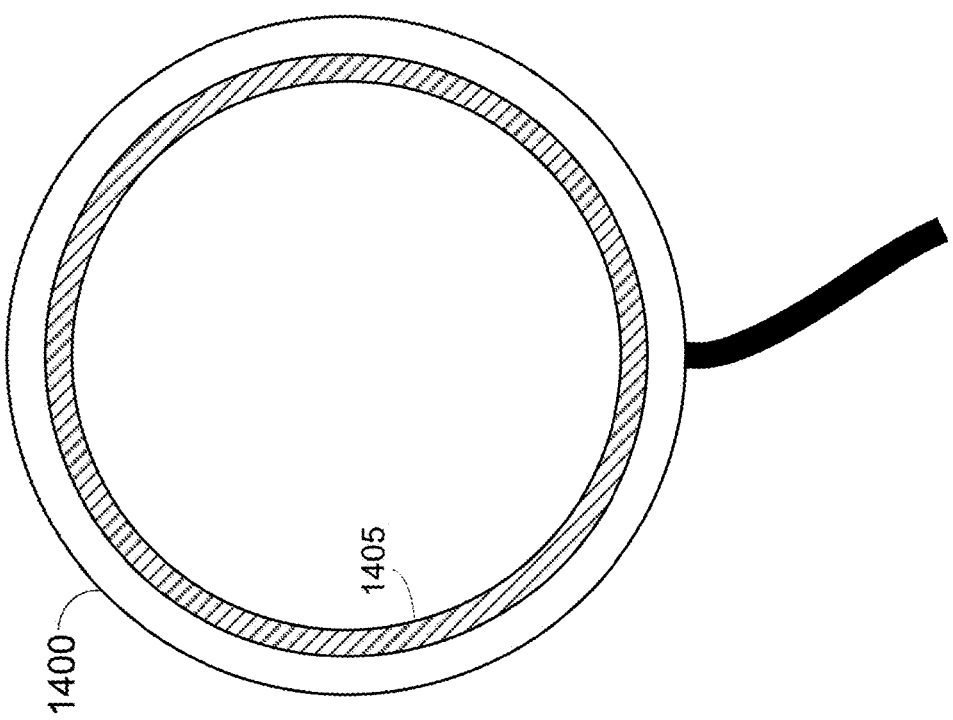

FIGS. 14A and 14B illustrate various configurations for an electric field (e-field) proximity sensor. An e-field sensor measures changes in electrical field properties to determine object location. Such a sensor can be used in concert with an existing capacitive electrode such as the ECG electrodes as described herein. The e-field sensors can be configured to measure changes in the electrical field produced during normal operation of the electrode. In such an arrangement, properties measured during normal contact with the patient's skin can be used to calibrate the e-field sensor.

An e-field sensor can be configured to output a variable value that is indicative of what portion of the sensor is detecting a change in an electrical field. As such, this can allow for various configurations of the e-field sensor as shown in FIGS. 14A and 14B. For example, as shown in FIG. 14A, an electrode 1400 can include a ring-shaped e-field sensor 1405. As noted above, when using a capacitive sensor, changes in measured capacitance at various points on the surface of the capacitive sensor can be used to measure position and amount of contact with, for example, a patient's skin. A similar concept is used with the ring-shaped e-field sensor 1405 where contact can be measured about the periphery of the electrode 1400. The electrode 1400 can have a capacitive surface that is machined such that a channel is defined therein. In certain implementations, the capacitive surface can be a plastic sheet coated with a conductive material such as Indium Tin oxide. However, it should be noted that this is merely shown by way of example and additional materials such as copper, stainless steel, tantalum, and other similar conductive materials can be used. The e-field sensor 1405 can then be inserted into the channel such that the e-field sensor 1405 is flush with the surface of the electrode 1400 that is against the patient's skin. Such a design can be used to measure amount of contact with a patient's skin by measuring a percentage of the circumference of the ring-shaped e-field sensor 1405 that is in contact with the patient's skin.

FIG. 14B illustrates an alternative design for an e-field based falloff sensing scheme. An electrode 1410 can be machined such that a checkerboard or hash-mark shaped inset is provided therein. An e-field sensor 1415 can be fitted into the inset of the electrode 1410 such that the e-field sensor sits flush with the surface of the electrode 1400 that is in contact with a patient's skin. The electrode 1410 can be a plastic sheet coated with a conductive material such as Indium Tin oxide. However, it should be noted that this is merely shown by way of example and additional materials such as copper, stainless steel, tantalum, and other similar conductive materials can be used.

Figure 15:
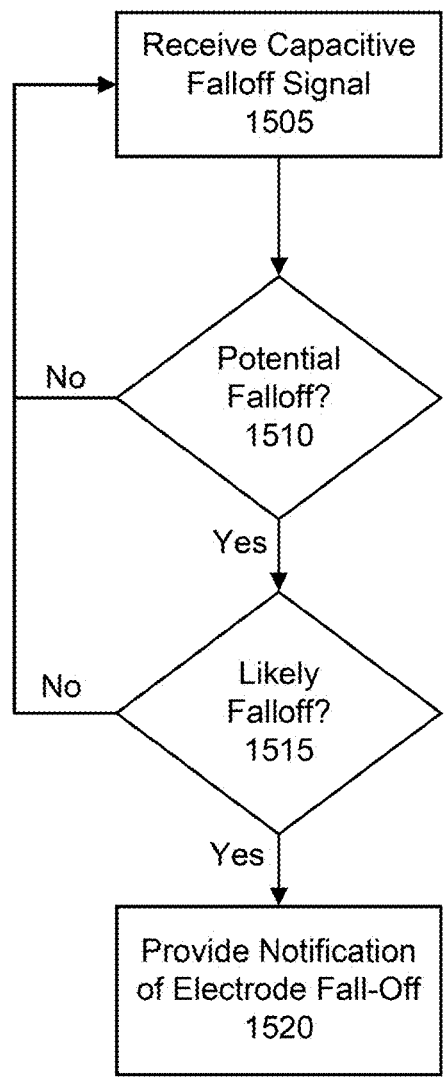
FIG. 15 depicts a process flow for determining a falloff event in an electrode having one or more capacitive sensors, in accordance with an example of the present disclosure.

Referring to FIG. 15, the electrode falloff detector can be configured to receive 1505 the measured capacitive falloff signal from, for example, one or more of the electrodes. In certain implementations, each electrode can be operably connected to a node such as connection pod 130 as shown in FIG. 1. The node can include processing circuitry configured to concatenate, multiplex, or otherwise combine the capacitive falloff signals from each of the electrodes into a single combined capacitive falloff signal for transmission to the medical device controller. In such an example, the electrode falloff device can be configured to receive 1505 the combined capacitive falloff signal, divide the combined capacitive falloff signal into individual components related to the individual electrodes, and process the individual components to determine whether one or more falloff events have occurred. Thus, in this example, the remainder of the process as shown in FIG. 15 can be repeated for each individual electrode that is associated with the combined capacitive falloff signal.

In some implementations, each electrode can have a direct connection to the medical device controller. For example, the medical device controller can include one or more external connectors into which one or more electrodes can be directly connected. In such an example, the electrode falloff detector can be configured to receive 1505 the capacitive falloff signals directly from the individual electrodes. Thus, in this example, the entirety of the process as shown in FIG. 15 can be repeated for each electrode operably connected to the electrode falloff detector.

Referring again to FIG. 15, the electrode falloff detector can be further configured to determine 1510 whether there has been potential falloff event at an electrode. For example, the capacitive falloff signal can indicate a change in a patient's measured capacitance (e.g., the patient's measured dielectric value) at a particular electrode. If the electrode falloff detector determines 1510 that there has not been a potential falloff (e.g., no indicated change in the capacitive falloff signal), the electrode falloff detector can receive 1505 an updated measured capacitive falloff signal.

Conversely, if the electrode falloff detector does determine 1510 that there has been a potential falloff event (e.g., there has been a measured change in a patient's dielectric value), the electrode falloff detector can further determine 1515 whether a falloff event has likely occurred. The electrode falloff detector can be further configured to determine 1515 whether the measured capacitance change was within an allowed threshold. Based upon various measured patient parameters and/or operating parameters of the medical device controller and the electrode falloff detector, a certain threshold of capacitance change can be determined as acceptable. In certain implementations, the medical device controller can include a baseline capacitance value or measurement for the patient. For example, the medical device controller can include a baseline dielectric value of 0.1 S/m for the patient. The acceptable threshold can be set as plus or minus a certain number of degrees from the baseline dielectric value. For example, the acceptable threshold can be set as plus or minus 0.01 S/m for a particular patient. If the electrode falloff detector determines 1515 that a dielectric value change at an electrode falls within the acceptable threshold, the electrode falloff detector can receive 1505 an updated capacitive falloff signal and repeat the process as shown in FIG. 15. Conversely, if the electrode falloff detector determines 1515 that a falloff event likely occurred, the electrode falloff detector can provide 1520 a notification of the likely falloff event.

In certain implementations, the electrode falloff detector can provide 1520 an alarm to the patient indicating a potential falloff event. For example, the alarm can include a visual alarm, an audio alarm, a tactile alarm, a combination of alarms (e.g., alarms that are in a predefined sequence or that overlap, such as, first, initiating a tactile alert, second, initiating an audible alert, and third, initiating a visual alert on the display), or another similar alarm configured to provide an indication or notification of the potential falloff event to the patient wearing the medical device. In certain implementations, an alarm manager (e.g., alarm module 326 as described above) can be configured to output one or more alarms in response to a specific event occurring. For example, if a treatable cardiac event is detected, the alarm manager can be configured to cause a high volume audible alarm to occur. In some examples, a high volume audible alarm can be about 80 db as measured 1 meter from the output device (e.g., a speaker or audio resonator). In the event of an electrode falloff detection, the alarm manager can be configured to output a lower volume alarm. For example, the alarm manager can be configured to output an alarm about 6-12 db lower than the high volume alarm (e.g., an alarm ranging from 68-74 db). In some examples, the alarm manager can be configured to output a visual alarm. For example, the alarm manager can flash a message or notification on the medical device's screen (e.g., touchscreen 220 as described above) or another similar visual output device such as one or more LED outputs. In certain implementations, the alarm manager can be configured to provide a tactile alarm as a standalone alarm or in combination with one or more of the audio and visual alarms.

In addition to providing the patient notification of the potential electrode falloff, the electrode falloff detector can further provide 1520 a notification to a remote server or monitoring service of the potential falloff. For example, the wearable medical device can be operably connected to a remote server (e.g., remote server 322 as described above) and can be configured to regularly transmit data indicative of a patient's cardiac activity as well as any detected events that occur while the patient is wearing the medical device. Upon detection of a potential electrode falloff, the electrode falloff detector can provide 1520 a notification such as a time/date stamp and an associated flag indicative of the potential falloff event. Upon review of the patient's information (e.g., by a technician or a patient's physician) collected by the remote server, the potential falloff event can be reviewed as well. In certain implementations, a high amount of falloff events (e.g., more than 5 every 2 hours) can be indicative that the patient needs to have their wearable medical device adjusted or replaced.

In an example of the process as shown in FIG. 15, the electrode falloff detector can determine that, over a series of signals representing 30 seconds in time, a patient's dielectric value at a specific electrode has dropped from 0.11 S/m to 0.09 S/m. As this drop falls within a 0.015 S/m threshold of a baseline value (e.g., a baseline value of 0.1 S/m), the electrode falloff detector can determine that there has not been a falloff event. To provide higher accuracy of whether a falloff event has occurred, the electrode falloff detector can compare measurements from multiple electrodes. For example, if a dielectric value change (e.g., 0.01 S/m) is consistently measured across multiple electrodes, the electrode falloff detector can label the dielectric change as a change in patient's body conditions rather than a falloff event. Such labels can be recorded in memory as flags, dielectric events, or other similar events for review later by, for example, a technician or other person (such as a physician) reviewing patient-related information recorded by the wearable medical device.

It should be noted that the thresholds (e.g., for dielectric measurements) used for capacitance-based falloff detection can be determined individually for each patient using the wearable medical device. For example, a patient can participate in a baselining process including measuring the patient's dielectric value during, for example, a garment fitting for the wearable medical device when the patient is first subscribed the device. Additionally, the patient can be instructed to perform a physical activity such as a six-minute walk test to measure how the patient's dielectric value changes during physical activity (e.g., due to sweat or changes in body temperature). In such an example, the thresholds can be dynamically alterable for a patient depending upon whether the patient is engaged in physical activity. Additional information such as accelerometer information can also be measured during the physical activity to determine what measurable parameters and characteristics are associated with the patient during physical activity.

It should be noted that a dielectric-based capacitive sensor and an electrostatic-based touch panel are shown by way of example only. Additional capacitance sensors such as resistive-based capacitance sensors can be used. For example, a resistive-based capacitive sensor includes a dynamically changing resistor that has a variable resistance based upon a capacitance level surrounding the resistor. A small current (e.g., 5 mA) can be passed through the resistive-based capacitive sensor. As the capacitance around the resistive-based capacitive sensor changes, the resistance changes in a linear manner. As such, by measuring the voltage change across the resistive-based capacitive sensor, the processing circuit can determine a capacitive falloff signal for further analysis by the electrode falloff detector.

Additionally, a Schering Bridge can be used to measure capacitance values at an electrode. Any changes in the measured values can be indicative of a falloff event. A Schering Bridge is an AC bridge circuit that produces a balanced capacitive measurement that is independent of frequency. As such, if frequency changes at the electrode-skin interface as a result of bio-electrical changes in the patient's body, an increase of perspiration between the electrode and the patient's skin, or other similar events that can cause a change in measured frequency, the output of the Schering Bridge remains balanced. However, if a falloff event occurs, the two halves of the Schering Bridge will become unbalanced (as a result of the increase in impedance resulting from the falloff event), thereby producing an output that can be indicative of the falloff event.

In certain implementations, frequency modulation can be used to measure capacitance changes at an electrode. By using known signal phase and amplitude, a received signal can be divided into various segments having different frequencies. One or more frequencies of interest can then be analyzed to reduce or eliminate noise that can impact measuring and detecting a falloff event. In other examples, synchronous demodulation can be implemented into a falloff detection scheme. In certain implementations, synchronous demodulation uses a diode rectifier to eliminate sideband information from a signal, thereby resulting in a low-noise carrier band signal for further analysis.

Optical-Based Falloff Event Detection

Figure 16:
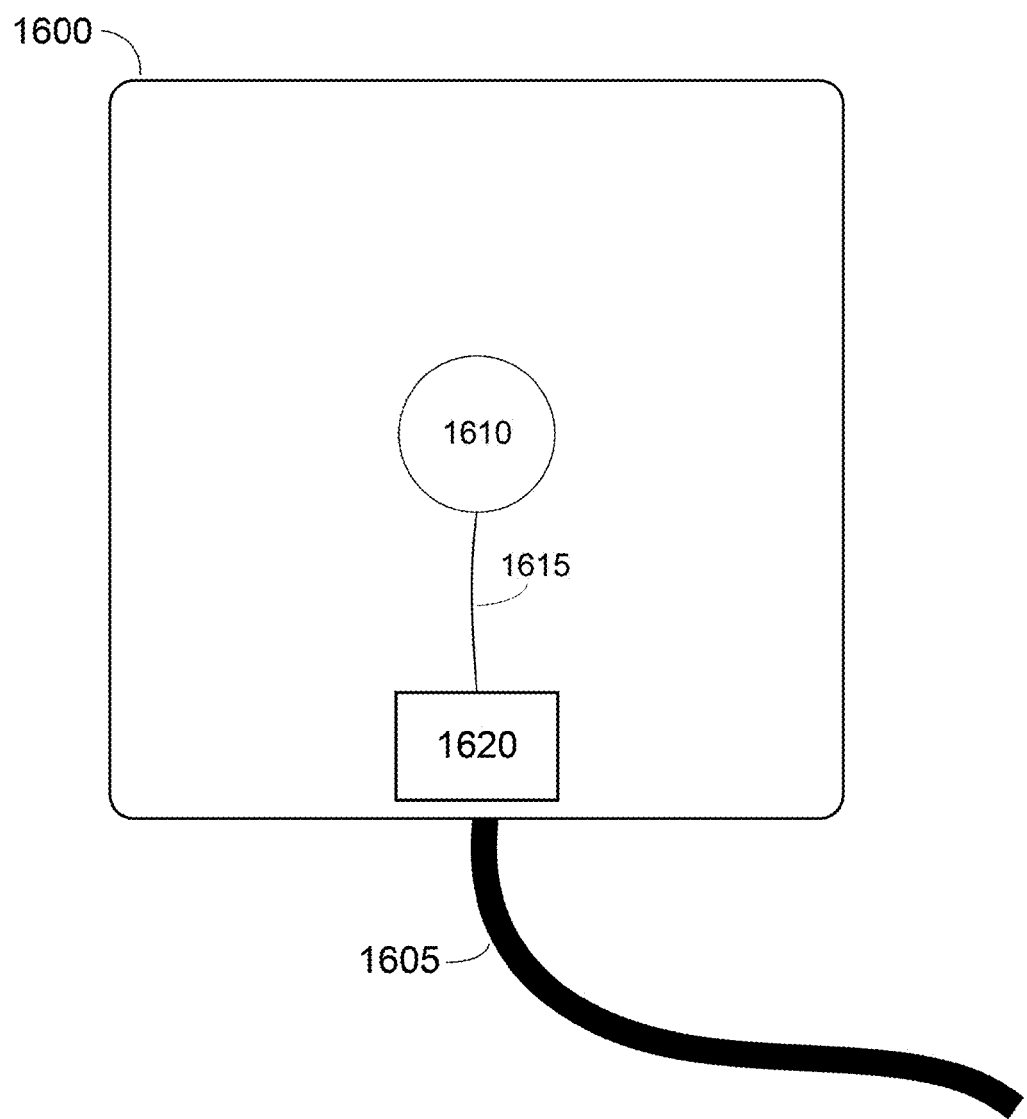
FIG. 16 depicts an electrode including one or more optical sensors, in accordance with an example of the present disclosure.
Figure 17:
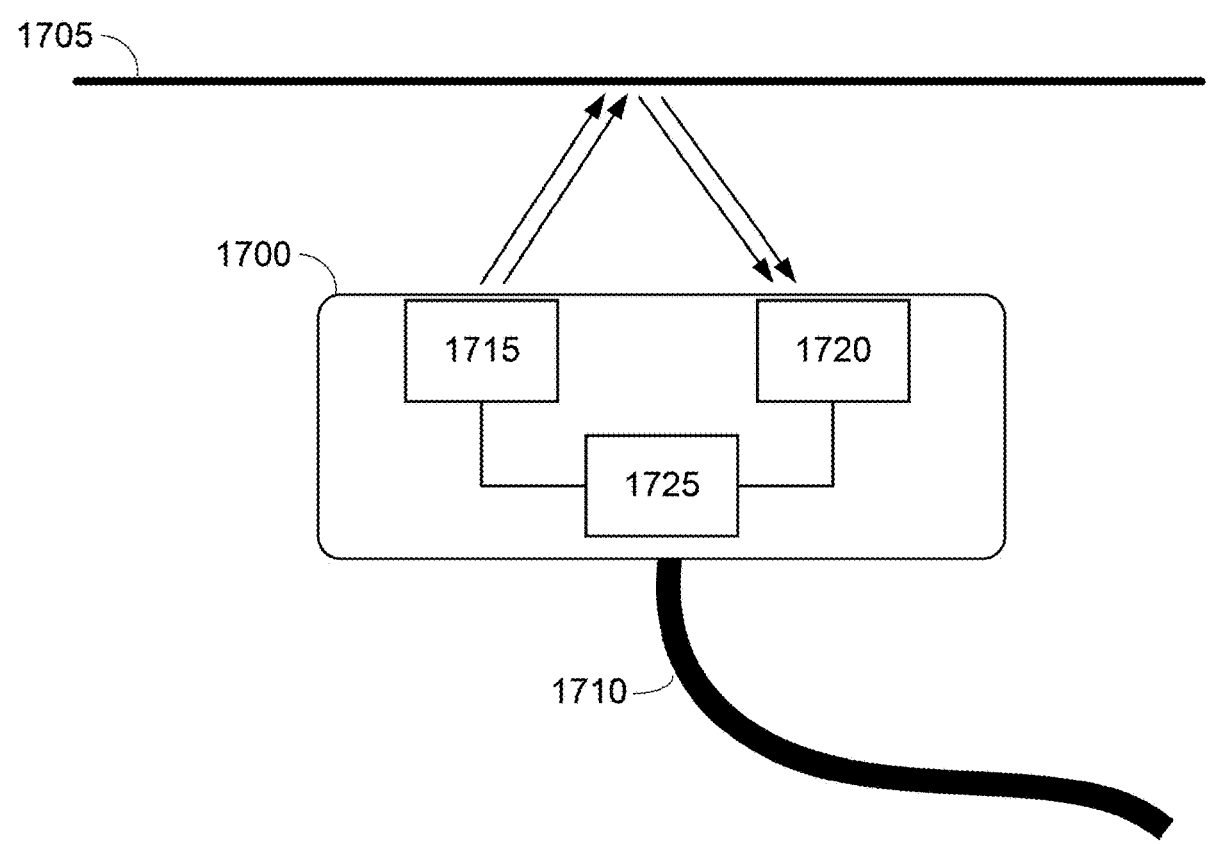
FIG. 17 depicts a sample circuit diagram for an optical sensor, in accordance with an example of the present disclosure.
Figure 18:
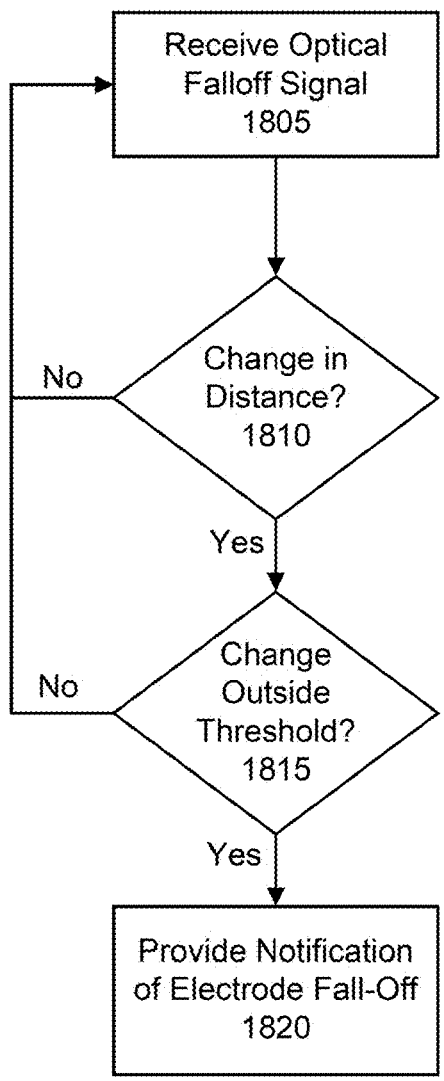
FIG. 18 depicts a process flow for determining a falloff event in an electrode having one or more optical sensors, in accordance with an example of the present disclosure.

In another example, as illustrated in FIGS. 16-18, an optical-based falloff detection scheme can be included in a wearable medical device. In such a scheme, one or more optical sensors can be integrated into the electrodes. A processing circuit can also be implemented into the electrodes such that output from the optical sensors can be processed (e.g., conditioned and filtered) prior to the medical device controller receiving the optical sensor outputs for further processing. In such an example, the medical device controller can monitor the optical sensor outputs for all the electrodes simultaneously (or, depending upon processing capabilities, substantially simultaneously) to detect an electrode falloff e.g., when some or all of the conductive portion of the sensing electrode loses contact with the patient's skin. For example, the optical sensors can be configured to both emit an optical signal and receive a reflected signal from the patient's skin. By analyzing properties of the received signal, and comparing the received signal to the transmitted signal, a processing circuit can determine a distance measurement between the optical sensor and the patient's skin. The medical device controller, or a component of the medical device controller such as the electrode falloff detector, can receive an optical falloff signal including distance measurement and change information, process the information to determine whether the sensor has likely fallen off, and provide a notification to a patient (e.g., via an alarm or by displaying a message on a display device such as touch screen 220 as described above) that the sensor has likely fallen off. The medical device controller can then instruct the patient to check the specific electrode and verify that the electrode is making proper connection with the patient's skin. The following discussion of FIGS. 16-18 provides additional details related to electrode falloff detection using optical sensors.

FIG. 16 illustrates a sample electrode 1600 that uses an optical-based falloff detection process. It should be noted that, as shown in FIG. 16, the electrode 1600 can be an electrode having at least one side configured to be placed against a patient's skin. For example, the electrode 1600 can be either a sensing electrode or a therapy electrode as described above. The electrode 1600 can be electrically coupled to a wire 1605 configured to carry signals such as physiological signals measured by the electrode 1600 to another device such as connection pod 130 or controller 120 as described above in reference to FIG. 1. For explanatory purposes only, wire 1605 as described herein can be configured to bi-directionally carry signals between the electrode 1600 and a medical device controller.

The electrode 1600 can include, for example, an optical sensor 1610. In certain implementations, the optical sensor 1610 can be a photoelectric sensor configured to both emit electromagnetic radiation as well as receive electromagnetic radiation (e.g., radiation reflected by a surface such as the patient's skin). In certain embodiments, the electromagnetic radiation can be visible light. In other examples, the electromagnetic radiation can be non-visible light such as infrared light and ultraviolet light. The optical sensor 1610 can be operably connected to a processing circuit 1620 by connection 1615. In such an example, connection 1615 can be a copper (or another similarly conductive material) wire configured to carry an electrical signal generated by the optical sensor 1610 to the processing circuit 1620. Processing circuit 1620 can then further process the electrical signal generated by the optical sensor 1610 and transmit the processed signal through wire 1605 to a medical device controller such as controller 120 as described above.

Depending upon the implementation of the electrode 1600, the processing circuit 1620 can be implemented in various manners. For example, the processing circuit 1620 can be a standalone processing device configured to receive an analog signal from the optical sensor 1610, amplify and convert the analog signal to a digital signal for transmission to a controller over the wire 1605. In certain implementations, the processing circuit 1620 can be implemented as a direct conversion analog-digital converter configured to generate a digital code for a specific voltage range received from the optical sensor 1610. The processing circuit 1620 can be configured to transmit the digital code over wire 1605 to the medical device controller for further processing.

In a specific example, a photoelectric optical sensor can be used to measure a distance between an electrode and a patient's skin. FIG. 17 illustrates a sample circuit diagram for a photoelectric optical sensor 1700 that can be operably connected to, for example, a processing circuit (e.g., processing circuit 1620 as shown in FIG. 16) via connector 1710 (similar to connection 1615 as shown in FIG. 16). In certain implementations, the photoelectric optical sensor 1700 will be positioned in contact with, or substantially adjacent to, a patient's skin 1705. For example, depending upon the design of the electrode and the placement of the photoelectric optical sensor 1700, a small gap between approximately 0.01 mm and 0.1 mm can be between the photoelectric optical sensor 1700 and the patient's skin 1705. In certain implementations, the photoelectric optical sensor 1700 can be slightly inset into the electrode, thereby having a distance of approximately 0.05 mm when the electrode is in contact with the patient's skin 1705.

Referring again to FIG. 17, the photoelectric sensor 1700 can include a light transmitting component 1715. In certain implementations, the light transmitting component 1715 can be a light emitting diode configured to emit a focused beam of light in a particular direction (indicated, for example, by the arrows pointing toward the patient's skin in FIG. 17). The photoelectric sensor 1700 can also include a light receiving component 1720. In certain implementations, the light receiving component 1720 can include a photodiode configured to receive reflected light that has bounced or otherwise been reflected back toward to the light receiving component 1720 (indicated, for example, by the arrows pointing away from the patient's skin in FIG. 17). In certain implementations, the photoelectric sensor 1700 can further include a filter 1725. For example, the filter 1725 can include a bandpass filter configured to filter the reflected light received by the light receiving component 1720 such that only light at frequencies corresponding to light reflected off skin are transmitted to, for example, processing circuit 1620 as shown in FIG. 16.

Referring to FIG. 18, the electrode falloff detector can be configured to receive 1805 the measured optical falloff signal from, for example, one or more of the electrodes. In certain implementations, each electrode can be operably connected to a node such as connection pod 130 as shown in FIG. 1. The node can include processing circuitry configured to concatenate, multiplex, or otherwise combine the optical falloff signals from each of the electrodes into a single combined optical falloff signal for transmission to the medical device controller. In such an example, the electrode falloff device can be configured to receive 1805 the combined optical falloff signal, divide the combined optical falloff signal into individual components related to the individual electrodes, and process the individual components to determine whether one or more falloff events have occurred. Thus, in this example, the remainder of the process as shown in FIG. 18 can be repeated for each individual electrode that is associated with the combined optical falloff signal.

In some implementations, each electrode can have a direct connection to the medical device controller. For example, the medical device controller can include one or more external connectors into which one or more electrodes can be directly connected. In such an example, the electrode falloff detector can be configured to receive 1805 the optical falloff signals directly from the individual electrodes. Thus, in this example, the entirety of the process as shown in FIG. 18 can be repeated for each electrode operably connected to the electrode falloff detector.

Referring again to FIG. 18, the electrode falloff detector can be further configured to determine 1810 whether there has been any change in measured distance between an optical sensor and the patient's skin at an electrode. For example, the optical falloff signal can indicate an updated distance measurement for the measured distance between the patient's skin and the optical sensor. If the electrode falloff detector determines 1810 that there has not been a change in the measured distance (e.g., no indicated change in the optical falloff signal), the electrode falloff detector can receive 1805 an updated measured optical falloff signal.

Conversely, if the electrode falloff detector does determine 1810 that there has been a change in the measured distance in the optical falloff signal, the electrode falloff detector can further determine 1815 whether the measured distance is outside of an accepted threshold. Based upon a position of the optical sensor relative to a skin-contacting surface of the electrode, a certain threshold of measured distance can be determined as acceptable. In certain implementations, the medical device controller can include a baseline acceptable distance measurement for the patient. For example, the medical device controller can include an acceptable threshold of less than 0.5 mm. If the electrode falloff detector determines 1815 that a measured distance between the optical sensor and a patient's skin at an electrode falls within the acceptable threshold, the electrode falloff detector can determine that no falloff event has occurred and can receive 1805 an updated optical falloff signal, thereby repeating the process as shown in FIG. 18. Conversely, if the electrode falloff detector determines 1815 that the measured distance between the optical sensor and a patient's skin is outside of the accepted threshold, the electrode falloff detector can provide 1820 a notification of the likely falloff event.

In certain implementations, the electrode falloff detector can provide 1820 an alarm to the patient indicating a potential falloff event. For example, the alarm can include a visual alarm, an audio alarm, a tactile alarm, a combination of alarms (e.g., alarms that are in a predefined sequence or that overlap, such as, first, initiating a tactile alert, second, initiating an audible alert, and third, initiating a visual alert on the display), or another similar alarm configured to provide an indication or notification of the potential falloff event to the patient wearing the medical device. In certain implementations, an alarm manager (e.g., alarm module 326 as described above) can be configured to output one or more alarms in response to a specific event occurring. For example, if a treatable cardiac event is detected, the alarm manager can be configured to cause a high volume audible alarm to occur. In some examples, a high volume audible alarm can be about 80 db as measured 1 meter from the output device (e.g., a speaker or audio resonator). In the event of an electrode falloff detection, the alarm manager can be configured to output a lower volume alarm. For example, the alarm manager can be configured to output an alarm about 6-12 db lower than the high volume alarm (e.g., an alarm ranging from 68-74 db). In some examples, the alarm manager can be configured to output a visual alarm. For example, the alarm manager can flash a message or notification on the medical device's screen (e.g., touchscreen 220 as described above) or another similar visual output device such as one or more LED outputs. In certain implementations, the alarm manager can be configured to provide a tactile alarm as a standalone alarm or in combination with one or more of the audio and visual alarms.

In addition to providing the patient notification of the potential electrode falloff, the electrode falloff detector can further provide 1820 a notification to a remote server or monitoring service of the potential falloff. For example, the wearable medical device can be operably connected to a remote server (e.g., remote server 322 as described above) and can be configured to regularly transmit data indicative of a patient's cardiac activity as well as any detected events that occur while the patient is wearing the medical device. Upon detection of a potential electrode falloff, the electrode falloff detector can provide 1820 a notification such as a time/date stamp and an associated flag indicative of the potential falloff event. Upon review of the patient's information (e.g., by a technician or a patient's physician) collected by the remote server, the potential falloff event can be reviewed as well. In certain implementations, a high amount of falloff events (e.g., more than 5 every 2 hours) can be indicative that the patient needs to have their wearable medical device adjusted or replaced.

In an example of the process as shown in FIG. 18, the electrode falloff detector can determine that, for a specific optical falloff signal, a particular electrode is approximate 0.1 mm from the patient's skin. As this measurement is within an acceptable threshold of 0.5 mm, the electrode falloff detector can determine that no falloff event has occurred. If, for an updated optical falloff signal, the measured distance between the particular electrode and the patient's skin is 1.2 mm, the electrode falloff detector can determine and provide an indication that a falloff event has likely occurred.

It should be noted that a photoelectric-based optical sensor as described above is shown by way of example only. Additional optical sensors can be incorporated for use in detecting a falloff event using optical sensors. For example, an infrared-based proximity sensor can be incorporated into an electrode. Similar to the photoelectric sensor, an infrared proximity sensor transmits an infrared signal that is reflected by a target object and detected by an infrared detector. Based upon timing and positioning information related to the received signal, distance information between the infrared sensor and the target object can be determined.

In certain implementations, a pulse oximetry sensor can be used as an optical sensor for detecting a falloff event. In such an example, in addition to merely monitoring distance information, the pulse oximetry sensor can measure additional information related to the patient such as pulse rates and blood oxygen levels. Such information can be used by the medical device controller to determine other information about the patient such as whether the patient is conscious.

As discussed above, the optical sensors are described as measuring distance between two objects (e.g., between the optical sensor and a patient's skin). However, in certain implementations, an optical sensor can return a zero or undefined value for the distance measurement if, for example, the distance between the optical sensor and the patient's skin exceeds the optical sensor's nominal range, or the maximum distance the optical sensor can measure. In such an example, the electrode falloff detector can be programmed to immediately respond to a zero or undefined measurement as indicating a falloff event.

In additional implementations, alternative optical sensors can be implemented into an electrode. For example, a camera-based optical sensor or sensor assembly can be implemented. One or more light sources can be integrated into the optical sensor assembly at, for example, the center of an electrode. One or more cameras (e.g., arranged in a ring about the periphery of the electrode) can be configured to measure reflected light produced as a result of the one or more light sources reflecting off a surface such as the patient's skin. A high value for measured light reflection can be indicative of a space between the light source and the patient's skin, which can be interpreted as a falloff event. In alternative designs, multiple light sources can be positioned about the periphery of the electrode with one or more cameras or other light detectors positioned at or about the middle of the electrode. The light sources can each be configured to output a certain color or frequency of light such that each light source is identifiable. The one or more cameras can be configured to measure reflected light from the light sources. By analyzing the received light signals for its individual components, a processor can determine which portions of the electrode have lost contact with the patient's skin (e.g., identifying a partial falloff event that can be indicative of a poorly fitting garment, improper electrode placement, and other similar factors that can cause a falloff event).

Impedance-Based Falloff Detection

Figure 19:
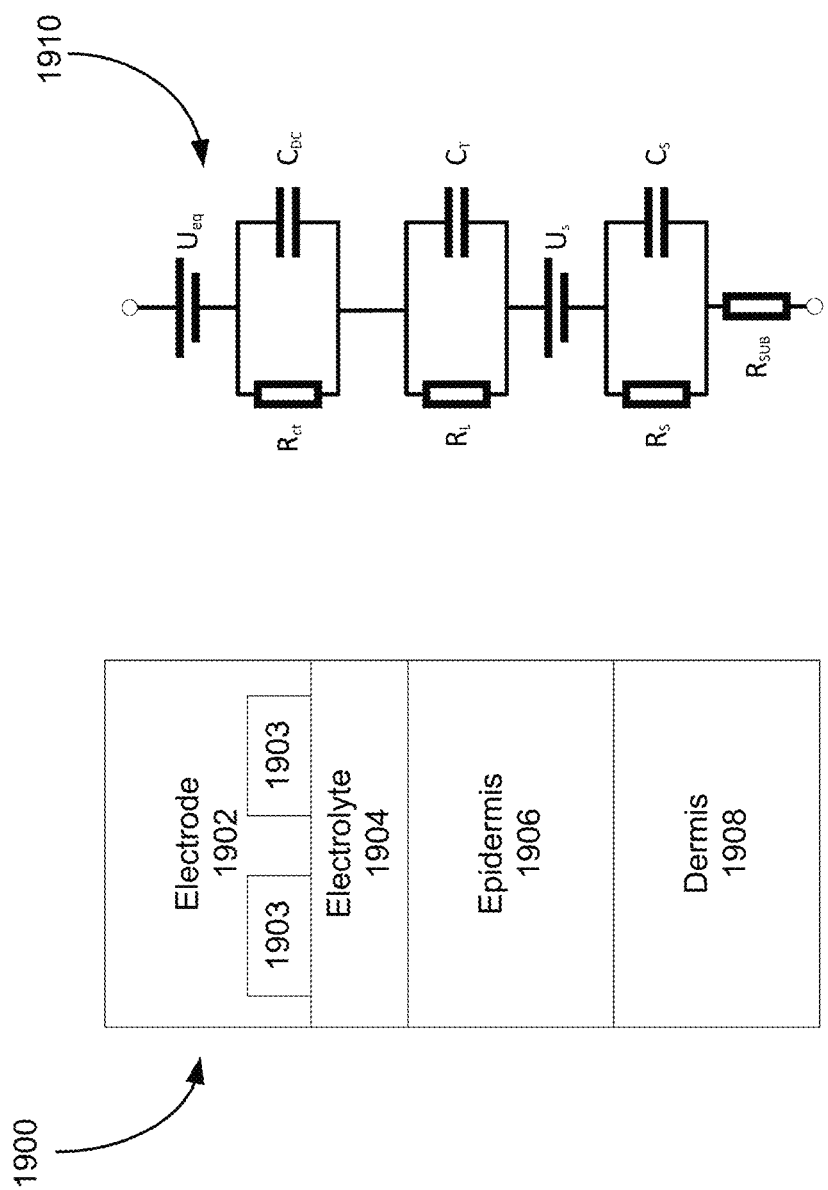
FIG. 19 depicts a sample electrode-skin interface and an equivalent circuit model, in accordance with an example of the present disclosure.
Figure 20:
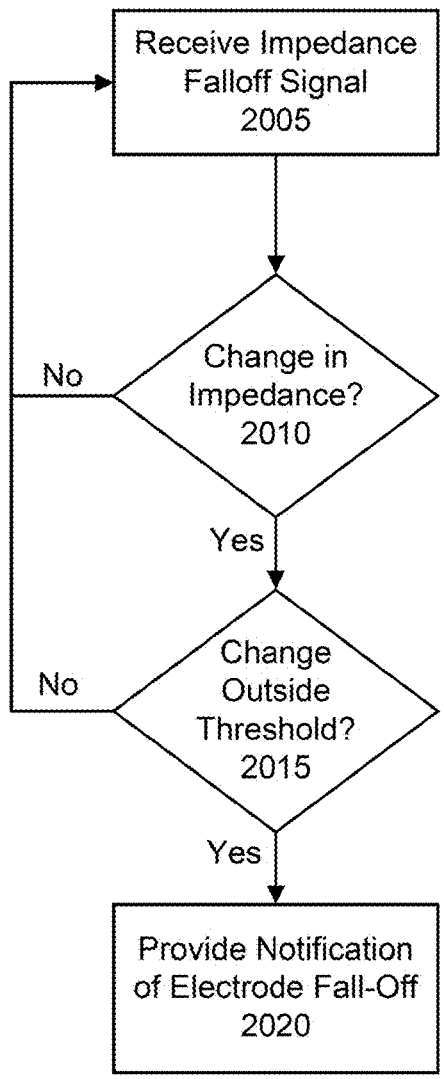
FIG. 20 depicts a process flow for determining a falloff event using as electrode-skin interface circuit model, in accordance with an example of the present disclosure.

In another example, as illustrated in FIGS. 19 and 20, an impedance-based falloff detection scheme can be included in a wearable medical device. In such a scheme, the existing capacitive measuring properties of a sensing and/or therapy electrode can be used to measure changes in impedance and/or capacitance between an electrode-skin interface, e.g., the area of contact between the sensing and/or therapy electrode and a patient's skin. In such an example, the medical device controller can monitor the outputs of each sensing electrode to determine changes in impedance that could be indicative of a falloff event, e.g., when some or all of the conductive portion of the electrode loses contact with the patient's skin.

The medical device controller, or a component of the medical device controller such as the electrode falloff detector, can receive an impedance falloff signal including a measurement of the current impedance at the sensor-skin interface for each electrode. Based upon the size of the electrode, and the total area of the electrode that is configured to contact the patient's skin, the electrode can be an impedance sensing electrode configured to measure a range of impedances. For example, the electrodes can be configured to measure between 50-200Ω, 200-400Ω, 400Ω-10 kΩ, 10 kΩ-1 MΩ, 1 MΩ-10 MΩ, 10 MΩ to 100 MΩ, 100 MΩ to 1 GΩ, and 1 GΩ to 10 GΩ. In certain implementations, a total impedance of the sensor-skin interface can be between 400Ω and 1 kΩ.

FIG. 19 illustrates a sample electrode-skin interface 1900 as well as an equivalent circuit model 1910. It should be noted that the electrode-skin interface 1900 as shown in FIG. 19 is directed to a dry electrode 1902 placed in direct contact with the patient's skin and configured to measure physiological signals such as ECG signals. For example, the electrode 1902 can be a capacitive-based sensing electrode including a tantalum conductive portion configured to be placed directly proximate to the patient's skin. In certain implementations, the electrode 1902 can include one or more isolated sensing areas or sensors 1903 disposed about the surface of the electrode 1902 and configured to measure an impedance value between the electrode 1902 and the patient's skin. The electrode-skin interface 1900 can include an electrolyte layer 1904. The electrolyte layer 1904 can include any liquids such as sweat that might be present on the patient's skin, as well as sweat and other liquids contained within the patient's skin. The electrode-skin interface 1900 can also include the epidermis 1906 positioned below the electrolyte layer 1904. The epidermis 1906 is the outermost layer of the patient's skin. It should be noted that the electrolyte layer 1904 and the epidermis 1906 can be physically present in the same layer of the patient's skin. However, for modeling purposes when measuring the impedance of an electrode-skin interface, it can be advantageous to model the two layers separately as they each have distinct electrical characteristics.

The epidermis layer 1906 provides a barrier for the human body against infection from various pathogens, as well as regulates the amount of water released by the body. The epidermis can vary in thickness, ranging from about 0.5 mm to about 1.5 mm depending upon what part of the body is being measured. The internal resistance of the epidermis can vary in accordance with the thickness of the epidermis.

As shown in FIG. 19, below the epidermis layer 1906 is the dermis layer 1908. The dermis is a layer of skin positioned between the epidermis and various subcutaneous tissues. The dermis includes various components such as hair follicles, sweat glands, lymphatic vessels and blood vessels. The dermis can also vary in thickness, ranging from about 0.6 mm to about 3.0 mm. Similar to the epidermis, the internal resistance of the dermis can vary in accordance with the thickness of the dermis.

In the sample electrode-skin interface 1900 as shown in FIG. 19, each specific layer of the interface can include unique and distinct electrical properties. For example, the epidermis layer 1906 can have an average impedance of approximately 1 kΩ. The electrolyte layer 1904, as a result of including a high number of conductive materials such as salt water, can have a low impedance as compared to the epidermis layer. For example, the electrolyte layer can have an impedance of less than 1Ω. Similarly, due to the presence of various sweat glands, blood vessels and other similar components, the dermis layer can have a lower impedance as compared to the epidermis layer. For example, the dermis layer can have an average impedance of approximately 500Ω. As such, the various layers of skin (i.e., the electrolyte layer 1904, the epidermis 1906, and the dermis 1908) can have an average combined impedance of about 1.5 kΩ. In certain implementations, depending upon various aspects specific to the patient wearing the sensing electrode (e.g., % body fat, amount of muscle, body temperature), the average combined impedance for each patient can vary. As such, the average combined impedance for a patient can range from approximately 1 kΩ to 100 kΩ. However, it should be noted that the above resistance and impedance numbers are provided by way of example only. Actual patient impedances can vary outside of the provided ranges as described above, and can be measured more accurately on a patient-by-patient basis.

When using an impedance-based falloff detection scheme, baseline values for various components in an electrical model can be determined and stored. Then, by using a set voltage and measured current at the sensing electrodes, the impedance at the electrode-skin interface can be modeled. Based upon a modeled value, a processing device, such as a medical device controller as described above, can determine a modeled impedance level at the sensing electrode and, based upon the determined impedance level, determine the likelihood that a falloff event has occurred. Electrical circuit model 1910 as shown in FIG. 19 can be used as a model for the various electrical properties of the electrode-patient interface 1900. In the circuit model 1910, $U_{eq}$ can represent the electrode potential, e.g., the voltage at the electrode. In certain implementations, the electrode potential can range from 2-12 v. For example, the electrode potential of the electrode can be 2.5 v. In the circuit model 1910, resistor $R_{ct}$ can represent the charge transfer resistance at the electrode-skin interface. For example, $R_{ct}$ provides a measurement of the actual resistance between the electrode and the patient's skin. By measuring changes in this value, the medical device controller can determine whether a falloff event has occurred, e.g., whether the electrode has lost contact with the patient's skin. The circuit model 1910 can also include capacitor $C_{DC}$ in parallel with resistor $R_{ct}$. Capacitor $C_{DC}$ can represent the capacitance of the sensing electrode. For example, capacitor $C_{DC}$ can be configured to be approximately 0.5-2 μF. In certain implementations, capacitor $C_{DC}$ can be configured to be approximately 1.0 μF.

The circuit model 1910 can also include a resistor $R_L$ and a capacitor $C_T$ positioned in parallel to each other, and the combination of the resistor $R_L$ and the capacitor $C_T$ can be positioned in series with the combination of resistor $R_{ct}$ and capacitor $C_{DC}$. Resistor $R_L$ can represent the resistance of the electrolyte layer (e.g., electrolyte layer 1904 as described above). As noted above, the electrolyte layer can have a resistance of approximately 1Ω. As such, resistor $R_L$ in the circuit model 1910 can have a resistance of approximately 1Ω. Capacitor $C_T$ can be configured to represent the capacitive behavior of the electrode-skin interface as a result of a lack of conductive material such as conductive gel. The capacitor $C_T$ can be configured to be about 0.1-0.5 pF. In certain implementations, the capacitor $C_T$ can be set to approximately 0.25 pF in the circuit model 1910.

The circuit model can also include a potential $U_S$ that represents the surface energy potential of the patient's skin. The energy potential $U_S$ can be positioned in the circuit model in series following the combination of resistor $R_L$ and the capacitor $C_T$. As noted above, electrical properties of a human's skin can vary greatly between individual bodies, but generally a human's potential energy at their skin (e.g., at the top of the dermis layer) is approximately 5-25 mV. Thus, for example, the energy potential $U_S$ can be set to approximately 10 mV in the circuit model 1910.

The circuit model 1910 can also include a resistor $R_S$ and a capacitor $C_S$ positioned in parallel to each other, and the combination of the resistor $R_L$ and the capacitor $C_T$ positioned in series with the energy potential $U_S$. Resistor $R_S$ can represent the resistance of the epidermis layer (e.g., epidermis layer 1906 as described above). As noted above, the epidermis layer can have a resistance of approximately 1 kΩ. As such, resistor $R_S$ in the circuit model 1910 can have a resistance of approximately 1 kΩ. Capacitor $C_S$ can be configured to represent the capacitive behavior of the dermis layer. The capacitor $C_S$ can be configured to be about 1-1.5 pF. In certain implementations, the capacitor $C_S$ can be set to approximately 1.25 pF in the circuit model 1910.

The model circuit 1910 can also include a resistor $R_{SUB}$ that represents the resistance of the dermis layer (e.g., dermis layer 1908). As shown in FIG. 19, the resistor $R_{SUB}$ can be positioned in series and following the combination of resistor $R_S$ and a capacitor $C_S$. As noted above, the dermis can have a resistance of approximately 500Ω. As such, resistor $R_{SUB}$ can have a resistance of approximately 500Ω.

As such, the circuit represented in circuit model 1910, has a combined resistance of approximately 1500Ω plus the impedance represented by resistor $R_{CT}$. Thus, for a set current being delivered to the skin by the electrode, a constant value can be modeled for the resistance across $R_{CT}$. For example, using a 1.0 mA current, an impedance of approximately 1 kΩ can be modeled for resistor $R_{CT}$. Thus, by monitoring any changes in the current provided by the sensing electrode at the electrode-skin interface, changes in the impedance between the sensing electrode and the patient's skin can be identified and, based upon the impedance changes, a falloff event can be determined.

It should be noted that the values used in the above description are provided by way of example only. For example, the sample values for current and voltage provided by the electrode are by way of example only and can be altered based upon various criteria such as type of sensing electrode being used, patient information such as % body fat, as well as baseline information from previous periods when the patient was being monitored.

FIG. 20 depicts a sample process flow for detecting an electrode falloff event using an impedance-based detection scheme. For example, an electrode falloff detector (e.g., electrode falloff detector 324 as shown in FIG. 3 and described above) can be configured to receive 2005 an impedance falloff signal from, for example, one or more of the electrodes. In certain implementations, the impedance falloff signal can include one or more modeled impedance measurements for resistor Rd as modeled using circuit model 1910.

In certain implementations, each electrode can be operably connected to a node such as connection pod 130 as shown in FIG. 1. The node can include processing circuitry configured to concatenate, multiplex, or otherwise combine the impedance falloff signals from each of the electrodes into a single combined impedance falloff signal for transmission to the medical device controller. In such an example, the electrode falloff device can be configured to receive 2005 the combined impedance falloff signal, divide the combined impedance falloff signal into individual components related to the individual electrodes, and process the individual components to determine whether one or more falloff events have occurred. Thus, in this example, the remainder of the process as shown in FIG. 20 can be repeated for each individual electrode that is associated with the combined impedance falloff signal.

In some implementations, each electrode can have a direct connection to the medical device controller. For example, the medical device controller can include one or more external connectors into which one or more electrodes can be directly connected. In such an example, the electrode falloff detector can be configured to receive 2005 the impedance falloff signals directly from the individual electrodes. Thus, in this example, the entirety of the process as shown in FIG. 20 can be repeated for each electrode operably connected to the electrode falloff detector.

Referring again to FIG. 20, the electrode falloff detector can be further configured to determine 2010 whether there has been any change in a modeled impedance value at an electrode-skin interface. For example, the impedance falloff signal can indicate an updated modeled impedance indicating that the impedance between the electrode and the patient's skin has either increased or decreased. If the electrode falloff detector determines 2010 that there has not been a change in the modeled impedance (e.g., no indicated change in the impedance falloff signal), the electrode falloff detector can receive 2005 an updated impedance falloff signal.

Conversely, if the electrode falloff detector does determine 2010 that there has been a change in the modeled impedance in the impedance falloff signal, the electrode falloff detector can further determine 2015 whether the modeled impedance is outside of an accepted threshold. In certain implementations, the medical device controller can include a baseline acceptable impedance. For example, the medical device controller can include an acceptable threshold of between 500Ω and 2.5 kΩ. At room temperature, the resistivity of air is approximately $2\times10^{16}$Ω/m. As such, during a falloff event, the modeled impedance can be expected to increase greatly (e.g., to more than 10 MΩ) as there is a portion of air between the electrode and the patient's skin increasing the impedance. As such, the threshold of acceptable modeled impedances can be varied based upon the patient's body type while still being multiple orders of magnitude away from the impedance of air.

Additionally, the electrode falloff detector can also determine 2015 whether there has been a partial falloff of an electrode. As the modeled impedance is directly related to the amount of the electrode surface that is contact with the patient's skin, variations in the modeled impedance can indicate that there has been a partial falloff event (e.g., when only a portion of the sensing electrode has lost contact with the patient's skin). For example, a modeled impedance of 2.5 kΩ can indicate that approximately 50% of the electrode has lost contact with the patient's skin. Other modeled impedances can indicate a different percentage of an electrode has lost contact with the patient's skin. For example, various modeled impedances can indicate that approximately 20%-50% of the electrode has lost contact with the patient's skin, approximately 25%-75% of the electrode has lost contact with the patient's skin, and approximately 50%-80% of the electrode has lost contact with the patient's skin. In other implementations, the electrode falloff detector can be programed to only determine whether there is contact between the electrode and the patient's skin or not. In such an implementation, the electrode falloff detector can be programed to provide a simple yes/no response (e.g., yes the electrode and skin are in contact or no they are not).

If the electrode falloff detector determines 2015 that the modeled impedance between the electrode and a patient's skin at an electrode falls within the acceptable threshold, the electrode falloff detector can determine that no falloff event has occurred and can receive 2005 an updated impedance falloff signal, thereby repeating the process as shown in FIG. 20. Conversely, if the electrode falloff detector determines 2015 that the modeled impedance between the electrode and a patient's skin is outside of the accepted threshold, the electrode falloff detector can provide 2020 a notification of the likely falloff event or, as noted above, warn about a potential partial falloff event.

In certain implementations, the electrode falloff detector can provide 2020 an alarm to the patient indicating a potential falloff event. For example, the alarm can include a visual alarm, an audio alarm, a tactile alarm, a combination of alarms (e.g., alarms that are in a predefined sequence or that overlap, such as, first, initiating a tactile alert, second, initiating an audible alert, and third, initiating a visual alert on the display), or another similar alarm configured to provide an indication or notification of the potential falloff event to the patient wearing the medical device. In certain implementations, an alarm manager (e.g., alarm module 326 as described above) can be configured to output one or more alarms in response to a specific event occurring. For example, if a treatable cardiac event is detected, the alarm manager can be configured to cause a high volume audible alarm to occur. In some examples, a high volume audible alarm can be about 80 db as measured 1 meter from the output device (e.g., a speaker or audio resonator). In the event of an electrode falloff detection, the alarm manager can be configured to output a lower volume alarm. For example, the alarm manager can be configured to output an alarm about 6-12 db lower than the high volume alarm (e.g., an alarm ranging from 68-74 db). In some examples, the alarm manager can be configured to output a visual alarm. For example, the alarm manager can flash a message or notification on the medical device's screen (e.g., touchscreen 220 as described above) or another similar visual output device such as one or more LED outputs. In certain implementations, the alarm manager can be configured to provide a tactile alarm as a standalone alarm or in combination with one or more of the audio and visual alarms.

In addition to providing the patient notification of the potential electrode falloff, the electrode falloff detector can further provide 2020 a notification to a remote server or monitoring service of the potential falloff. For example, the wearable medical device can be operably connected to a remote server (e.g., remote server 322 as described above) and can be configured to regularly transmit data indicative of a patient's cardiac activity as well as any detected events that occur while the patient is wearing the medical device. Upon detection of a potential electrode falloff, the electrode falloff detector can provide 2020 a notification such as a time/date stamp and an associated flag indicative of the potential falloff event. Upon review of the patient's information (e.g., by a technician or a patient's physician) collected by the remote server, the potential falloff event can be reviewed as well. In certain implementations, a high amount of falloff events (e.g., more than 5 every 2 hours) can be indicative that the patient needs to have their wearable medical device adjusted or replaced.

In the above discussion, a circuit model for modeling impedance has been described. However, this circuit model is provided by way of example only. In additional implementations, a circuit model can be created for modeling capacitance (e.g., the value of capacitor $C_{DC}$ as included in circuit model 1910). In such an example, the values for voltage, current and resistance can be fed into the model to model the capacitance at the electrode-skin interface. Additionally, various frequencies can be applied to the model. By using a known frequency, and varying the frequency over a range of frequencies, the capacitance of the electrode-skin interface can be modeled across the range of frequencies.

Combined Falloff Detection

The falloff detection schemes and processes as described above can be implemented as standalone options for falloff detection as well as part of a combined falloff detection scheme. For example, as noted above, if a patient is in a warm environment (e.g., where the ambient temperature is close to human body temperature), the temperature-based falloff detection process as described above may not immediately recognize all falloff events. Additionally, in certain implementations, the optical-based sensing can return a false indication of a falloff event. For example, if the patient's body is curved or bent such that only the portion of the electrode containing the optical sensor is away from the skin, but is still making good enough contact to provide a strong sensing signal (from a sensing electrode) or to provide a therapeutic shock (for a therapy electrode), the electrode falloff detector may register the event as a falloff event when the sensor is actually still properly positioned. By including the impedance falloff detection scheme as described above in addition to the optical sensor, the electrode falloff detector can then determine that at least a portion of the electrode is still in contact with the patient's skin.

As such, a combination of the above discussed falloff detection techniques can be implemented in a wearable medical device. For example, both temperature-based detection and capacitance-based detection sensors can be integrated into a single electrode. In such implementations, the electrode falloff detector can be configured to monitor both temperature changes as well as capacitance changes at each electrode. Similarly, optical-based falloff detection can be implemented with one or both of temperature-based falloff detection and capacitance-based falloff detection.

Additionally, the acceptable thresholds for determining a falloff event can be configured, programmed, or otherwise altered based upon the type of electrodes being used and their associated operating parameters, as well as the combinations of detection schemes being used.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed:

1. A system for detecting contact between an electrode and a skin of a patient, the system comprising:
   an electrode assembly comprising at least one sensing electrode configured to be disposed substantially proximate to the patient's skin and configured to sense a surface electrocardiogram (ECG) signal of the patient, wherein the at least one sensing electrode is configured to detect an impedance within an impedance detection range of 50Ω to 10 MΩ;
   one or more sensors disposed on the electrode assembly and isolated from the at least one sensing electrode, the one or more sensors configured to measure patient impedance indicative of contact between the at least one sensing electrode and the patient's skin; and
   a controller configured to
     determine baseline patient impedance information for the patient at an initial time period, the baseline patient impedance information being determined based upon a set voltage and measured current transmitted by the at least one sensing electrode to the patient and received by at least one of the one or more sensors,
     receive data representing the measured patient impedance from the one or more sensors,
     store a model electric circuit representative of an interface between the at least one sensing electrode and the patient's skin based upon the received data wherein at least one input to the model comprises at least a portion of the data representing the patient impedance, the electric circuit model electric circuit comprising
       a reactive portion configured to model one or more of capacitive and inductive properties of the interface between the at least one sensing electrode and the patient's skin, and
       a resistive portion configured to model resistive properties of the interface between the at least one sensing electrode and the patient's skin,
     adjust one or more of the reactive portion of the model electric circuit or the resistive portion of the model electric circuit based upon the baseline patient impedance information, receive an output from the model electric circuit, the output indicative of the patient impedance, cause the at least one sensing electrode to transmit the set voltage and measured current to the patient, receive updated data from the one or more sensors during a current monitoring period, the updated data indicating a measured response to the transmitted set voltage and measured current at the one or more sensors, determine model changes to one or more of the reactive portion of the model electric circuit or the resistive portion of the model electric circuit based upon the updated data, measure changes in the patient impedance based upon the output of the model electric circuit and the determined model changes, and determine, based at least in part on the received data and the changes in the patient impedance measured based upon the output of the model electric circuit and the determined model changes, that there has been a partial falloff of the at least one sensing electrode from the patient's skin wherein only a portion of the at least one sensing electrode has lost contact with the patient's skin.

2. The system of claim 1, further comprising an alarm module configured to output at least one alarm if the controller determines that there has been the partial falloff of the at least one sensing electrode from the patient's skin.

3. The system of claim 2, wherein the at least one alarm comprises at least one of an audio alarm, a visual alarm, a tactile alarm, and combinations thereof.

4. The system of claim 1, further comprising a network interface operably connected to the controller and configured to establish communication between the controller and a remote computing device such that, if the controller determines that there has been the partial falloff of the at least one sensing electrode from the patient's skin, a notification is sent to the remote computing device indicating the partial falloff.

5. The system of claim 1, wherein the one or more sensors are disposed on the at least one sensing electrode.

6. The system of claim 1, wherein the patient impedance defines a level of contact between the at least one sensing electrode and the patient's skin.

7. The system of claim 6, wherein the controller is further configured to compare the level of contact to a contact threshold level of contact to determine a falloff event.

8. The system of claim 1, wherein the model electric circuit is configured to simulate an impedance level between the electrode assembly and the patient's skin representative of the patient impedance, the model electric circuit further comprising at least a first cell configured to simulate a stored energy level of the at least one sensing electrode, a first capacitive and resistive pair configured to simulate the at least one sensing electrode, a second capacitive and resistance pair configured to simulate an electrolyte layer positioned between the at least one sensing electrode and the patient's skin, a second cell configured to simulate an energy potential between the at least one sensing electrode and the patient's skin, a third capacitive and resistance pair configured to simulate an epidermis layer of the patient, and a resistance configured to simulate a dermis layer of the patient.

9. The system of claim 1, wherein the one or more sensors are further configured to measure one or more properties including at least one of temperature, capacitance, measured distance between the at least one sensing electrode and a body of the patient, and oxygen saturation of blood of the patient.

10. The system of claim 1, wherein the one or more sensors comprise a combination of multiple sensor types selected from an impedance sensor and one or more of a temperature sensor, a capacitive sensor, or an optical sensor.

11. The system of claim 10, wherein the multiple sensor types are configured to operate in concert to provide multiple measurements of one or more properties determined by a position of the at least one sensing electrode in relation to a body of the patient.

12. The system of claim 11, wherein the controller is further configured to receive data representing the measured one or more properties from each of the multiple sensor types to determine whether the at least one sensing electrode is in contact with the patient's body.

13. The system of claim 1, further comprising a network interface configured to establish communication between the controller and a remote computing device, wherein the controller is configured to send a notification to the remote computing device indicating the partial falloff of the at least one sensing electrode.

14. The system of claim 1, wherein the controller is further configured to generate a notification that indicates a percentage associated with the partial falloff of the at least one sensing electrode.

15. A system for detecting contact between an electrode and a skin of a patient, the system comprising:

an electrode assembly comprising
a plurality of sensing electrodes configured to be disposed substantially proximate to the patient's skin and configured to provide outputs that (a) are indicative of electrocardiogram (ECG) activity of the patient, and (b) comprise a current provided by at least one of the plurality of sensing electrodes at an electrode-skin interface, and
at least one therapy electrode configured to provide one or more therapeutic pulses to the patient; and
a controller in electrical communication with the electrode assembly, the controller configured to
determine baseline patient impedance information for the patient at an initial time, the baseline patient impedance information being determined based upon a set voltage and measured current transmitted by the plurality of sensing electrodes to the patient and received by at least one of the at least one therapy electrode or one of the plurality of sensing electrodes,
measure, based on the outputs from the plurality of sensing electrodes, one or more patient impedance values indicating contact between one or more of the plurality of sensing electrodes and the patient's skin,
receive data representing the measured one or more patient impedance values indicating contact between the one or more of the plurality of sensing electrodes and the patient's skin,
store a model electric circuit representative of an interface between the one or more of the plurality of sensing electrodes and the patient's skin based upon the measured one or more patient impedance values, wherein at least one input to the model electric circuit comprises at least a portion of the measured one or more patient impedance values, the model electric circuit comprising
   a reactive portion configured to model one or more of capacitive and inductive properties of the interface between the one or more of the plurality of sensing electrodes and the patient's skin, and
   a resistive portion configured to model resistive properties of the interface between the one or more of the plurality of sensing electrodes and the patient's skin,
adjust one or more of the reactive portion of the model electric circuit or the resistive portion of the model electric circuit based upon the baseline patient impedance information,
receive an output from the model electric circuit, the output from the model electric circuit indicative of a level of contact between the at least one of the plurality of sensing electrodes and the skin of the patient,
cause at least one of the at least one therapy electrode or one of the plurality of sensing electrodes to transmit the set voltage and measured current to the patient,
receive updated data from the plurality of sensing electrodes during a current modeling period, the updated data indicating a measured response to the transmitted set voltage and measured current at the plurality of sensing electrodes,
determine model changes to one or more of the reactive portion of the model electric circuit or the resistive portion of the model electric circuit based upon the updated data,
measure changes in patient impedance based upon the output of the model electric circuit and the determined model changes,
determine, based at least in part on the data representing the measured one or more patient impedance values and the changes in patient impedance measured based upon the output of the model electric circuit and the determined model changes, that there has been a partial falloff of the one or more of the plurality of sensing electrodes from the patient's skin, and
measure an impedance level between the one or more of the plurality of sensing electrodes and the patient's skin based on the outputs indicative of ECG activity,
wherein the impedance level is in an impedance detection range of 50Ω to 10 MΩ.

16. The system of claim 15, the model electric circuit further comprising at least
   a first cell configured to simulate a stored energy level of the one or more of the plurality of sensing electrodes,
   a first capacitive and resistive pair configured to simulate the one or more of the plurality of sensing electrodes,
   a second capacitive and resistance pair configured to simulate an electrolyte layer positioned between the one or more of the plurality of sensing electrodes and the patient's skin,
   a second cell configured to simulate an energy potential between the one or more of the plurality of sensing electrodes and the patient's skin,
   a third capacitive and resistance pair configured to simulate an epidermis layer of the patient, and
   a resistance configured to simulate a dermis layer of the patient.

17. The system of claim 16, wherein the controller is configured to compare the level of contact to a contact threshold level of contact to determine a falloff event.

18. The system of claim 15, further comprising an alarm module operably configured to the controller and configured to output at least one alarm if the controller determines that there has been the partial falloff of the one or more of the plurality of sensing electrodes from the patient's skin.

19. The system of claim 18, wherein the at least one alarm comprises at least one of an audio alarm, a visual alarm, a tactile alarm, and combinations thereof.

20. The system of claim 15, further comprising a network interface operably connected to the controller and configured to establish communication between the controller and a remote computing device such that, if the controller determines that there has been the partial falloff of the one or more of the plurality of sensing electrodes from the patient's skin, a notification is sent to the remote computing device indicating the partial falloff.

21. The system of claim 15, further comprising one or more sensors selected from at least a temperature sensor, a capacitive sensor, and an optical sensor.

22. The system of claim 21, wherein the one or more sensors are configured to operate in concert to provide multiple measurements of one or more properties determined by a position of the one or more of the plurality of sensing electrodes in relation to the patient's skin.

23. The system of claim 22, wherein the controller is further configured to receive data representing the multiple measurements of the one or more properties to determine whether the one or more of the plurality of sensing electrodes is in contact with a body of the patient.

24. The system of claim 1, wherein the reactive portion of the model electric circuit comprises a capacitor network comprising one or more capacitive elements and the resistive portion of the model electric circuit comprises a resistor network comprising one or more resistive elements.

25. A system for detecting contact between an electrode and a patient's skin, the system comprising:
   an electrode assembly comprising an electrode configured to be disposed substantially proximate to a skin of a patient and configured to sense at least one surface ECG signal, wherein the electrode comprises an impedance detection range of 50Ω to 10 MΩ;
   one or more sensors disposed on the electrode assembly and isolated from the electrode, the one or more sensors configured to measure an impedance level between the electrode and the skin; and
   a controller configured to
      receive data representing the measured impedance level and determine, based at least in part on the received data, whether the electrode is in contact with the skin, wherein the measured impedance level defines a level of contact between the electrode and the skin,
      store a model electric circuit representative of an interface between the electrode and the skin, wherein at least one input to the model electric circuit comprises at least a portion of the received data, the model electric circuit comprising
         a reactive portion configured to model one or more of capacitive and inductive properties of the interface, and
         a resistive portion configured to model resistive properties of the interface and
      determine, based at least in part on the received data, that there has been a partial falloff of the electrode from the skin wherein only a portion of the electrode has lost contact with the skin.

26. The system of claim 25, further comprising an alarm module configured to output at least one alarm if the controller determines that there has been the partial falloff of the electrode from the skin.

27. The system of claim 25, further comprising a network interface configured to establish communication between the controller and a remote computing device such that, if the controller determines that there has been the partial falloff of the electrode from the skin, a notification is sent to the remote computing device indicating the partial falloff.

28. The system of claim 25, wherein:
the controller is further configured to compare the level of contact to a contact threshold level of contact to determine the partial falloff.

29. The system of claim 25, wherein the controller is further configured to determine that the electrode is improperly positioned with respect to the skin in response to the measured impedance level exceeding 10 MO.

* * * * *

UNITED STATES PATENT AND TRADEMARK OFFICE
CERTIFICATE OF CORRECTION

| | | |
|---|---|---|
| PATENT NO. | : 11,672,484 B2 | Page 1 of 1 |
| APPLICATION NO. | : 15/381206 | |
| DATED | : June 13, 2023 | |
| INVENTOR(S) | : Eric J Biel et al. | |

It is certified that error appears in the above-identified patent and that said Letters Patent is hereby corrected as shown below:

In the Claims

In Column 47, Line 20:
Please replace "MO" with --MΩ--.

Signed and Sealed this
Twenty-fifth Day of July, 2023

Katherine Kelly Vidal
*Director of the United States Patent and Trademark Office*